US008815563B2

(12) United States Patent
Davis et al.

(10) Patent No.: US 8,815,563 B2
(45) Date of Patent: Aug. 26, 2014

(54) MODIFIED VIRUS

(75) Inventors: Benjamin Guy Davis, Oxford (GB); Leonard William Seymour, Oxford (GB); Kerry Fisher, Oxford (GB)

(73) Assignee: PsiOxus Therapeutics Limited, London (GB)

( * ) Notice: Subject to any disclaimer, the term of this patent is extended or adjusted under 35 U.S.C. 154(b) by 2305 days.

(21) Appl. No.: 11/572,556

(22) PCT Filed: Jul. 18, 2005

(86) PCT No.: PCT/GB2005/002829
§ 371 (c)(1),
(2), (4) Date: Sep. 4, 2007

(87) PCT Pub. No.: WO2006/008513
PCT Pub. Date: Jan. 26, 2006

(65) Prior Publication Data
US 2008/0069802 A1 Mar. 20, 2008

(30) Foreign Application Priority Data
Jul. 23, 2004 (GB) .................................. 0416487.7

(51) Int. Cl.
*C12N 7/00* (2006.01)
*A01N 63/00* (2006.01)

(52) U.S. Cl.
USPC ....................................... 435/235.1; 424/93.6

(58) Field of Classification Search
None
See application file for complete search history.

(56) References Cited

U.S. PATENT DOCUMENTS

| | | | |
|---|---|---|---|
| 5,572,925 A | 11/1996 | Van Pay et al. | |
| 5,601,818 A | 2/1997 | Freeman et al. | |
| 5,631,236 A | 5/1997 | Woo et al. | |
| 5,677,178 A | 10/1997 | McCormick | |
| 5,698,443 A | 12/1997 | Henderson et al. | |
| 5,846,945 A | 12/1998 | McCormick | |
| 5,871,726 A | 2/1999 | Henderson et al. | |
| 6,127,197 A | 10/2000 | Kim et al. | |
| 6,248,516 B1 | 6/2001 | Winter et al. | |
| 6,291,158 B1 | 9/2001 | Winter et al. | |
| 2003/0064054 A1* | 4/2003 | Dong | 424/93.2 |

FOREIGN PATENT DOCUMENTS

| | | |
|---|---|---|
| EP | 0368684 | 5/1990 |
| WO | WO 96/30385 | 10/1996 |
| WO | WO 97/00492 | 1/1997 |
| WO | WO 97/01645 | 1/1997 |
| WO | WO 00/22136 | 4/2000 |
| WO | WO 00/22137 | 4/2000 |

OTHER PUBLICATIONS

Lazdins, I. et al., "Rotavirus antigenicity is affected by the gentic context and glycosylation of VP7", 1995, Virology, vol. 209:pp. 80-89.*

Contreras, J et al, Double Genetic Modification of Adenovirus Fiber With RGD Polylysine Motifs Significantly Enhances Gene Transfer to Isolated Human Pancreatic Islets, Transplantation, vol. 76, No. 1, 2003, pp. 252-261.

Caillet-Boudin M, et al, O-Linked GLCNAC in Serotype-2 Adenovirus Fiber, European Journal of Biochemistry, vol. 184, 1989, pp. 205-211.

Blanche, F et al, Polypeptide Composition of an Adenovirus Type 5 Used in Cancer Gene Therapy, Journal of Chromatography A, vol. 921, 2001, pp. 39-48.

Cauet et al., "Identification of the Glycosylation site of the Adenovirus Type 5 Fibre Protein," *Biochemistry* 2005, 44, 5453-5460.

Russell, "Adenoviruses: update on structure and function," *Journal of General Virology* (2009), 90, 1-20.

* cited by examiner

*Primary Examiner* — Michael Burkhart
(74) *Attorney, Agent, or Firm* — Banner & Witcoff, Ltd.

(57) ABSTRACT

Modified viral particles wherein the viral particles, typically adenoviral particles, are modified by glycosylation and the use of the modified viral particles to deliver heterologous nucleic acid to cells. Also disclosed are pharmaceutical compositions comprising the same and method of treatment using the same.

12 Claims, 16 Drawing Sheets

Figure 4C

UNMODIFIED

| RUN | ZAve | Error |
|---|---|---|
| 1 | 112.9 | 0.00332 |
| 2 | 123.4 | 0.002 |
| 3 | 122.4 | 0.0014 |

MODIFIED

| RUN | ZAve | Error |
|---|---|---|
| 1 | 231.9 | 0.0036 |
| 2 | 202.2 | 0.00847 |
| 3 | 177.8 | 0.00794 |

Figure 4D

| UNMODIFIED | | | UNMODIFIED | | |
|---|---|---|---|---|---|
| RUN | mV | Bandwidth(mV) | RUN | mV | Bandwidth(mV) |
| 1 | -29.5 | 28.7 | 1 | -43.7 | 25.6 |
| 2 | -15.7 | 25.1 | 2 | -47.9 | 37.1 |
| 3 | -19.2 | 17.1 | 3 | -31.7 | 40.8 |
| 4 | -14.9 | 30.5 | 4 | -29.8 | 69.9 |
| 5 | -14.3 | 15.2 | 5 | -51.9 | 38.1 |

MODIFIED VIRUS

FIELD OF THE INVENTION

The invention relates to modified viral particles wherein the viral particles, typically adenoviral particles, are modified by glycosylation and the use of the modified viral particles to deliver heterologous nucleic acid to cells.

BACKGROUND OF THE INVENTION

Gene therapy has applications in the treatment of infectious, vascular and multifactorial diseases and employs a variety of viruses each with specific qualities making them suitable for their chosen application [1]. Gene therapy includes several different strategies the first is described as gene supplementation therapy; that is to successfully supplement defective genes that cause disease, with wild type copies delivered to target cells, as in the case of cystic fibrosis [2]. The second is cell factory gene therapy, which uses DNA or RNA as a therapeutic for expression in irrelevant cells to treat deficiencies such as diabetes [3]. Third is treatment of tumours [4] which relies on delivering the DNA or RNA normally with the purpose of killing the target cell. Killing strategies can involve expression of cytotoxic agents, enzymes capable of activating produgs to toxic metabolites ("suicide enzymes") or immune-provoking proteins. Alternatively the use of a replication competent (or conditionally replicating) lytic viral vector can cause cell lysis. In addition there are other strategies—notably the encoding of hairpin RNA to produce small inhibitory RNA (siRNA) in situ to downregulate expression of target mRNA, encoding oligonucleotides to promote exon skipping, ribozymes and antisense strategies.

In all cases successful delivery of the gene delivery vector (which can be viral or synthetic) would be improved if the vector had selectivity for binding and entry into target cells.

Adenoviruses are widespread in nature, infecting birds, mammals and man. Belonging to the family Adenoviridae and the genus *Mastadenovirus*, over 50 human adenovirus serotypes have been classified within 6 subgenera (A-F), according to their hemaglutination pattern, their DNA homology and other criteria. The most prevalent serotypes are those of subgenus C (1, 2, 5 and 6). Together with some serotypes of subgenus B and E these viruses are a frequent cause of acute upper respiratory tract (URT) infections and other respiratory pathologies. In addition, Adenoviruses also cause a number of other types of infection often associated with the eye (e.g. conjunctivitis and epidemic keratoconjunctivitis), the gastrointestinal tract (e.g. gastroenteritis) or the urogenital tract (e.g. cystitis). The organ tropism is distinct for different human adenovirus subgenera. Adenoviruses have also been used therapeutically for vaccination and for gene therapy.

The adenovirus is an example of a virus typically used for gene therapy [5]. It has an icosahedral structure with 12 protruding fibre proteins, which possess a specifically folded arrangement of protein at the end called the knob domain that binds via a three-way interaction with the coxsackie adenovirus receptor (CAR) present on many cell membranes [6]. This is known to be the major route of infection, although alternative pathways involve binding of the virus to cell surface integrins and heparin sulphate proteoglycans [7]. Specific integrin mediated uptake is also known [7].

A preferred vector would combine powerful ability for transgene expression with a high level of cell or tissue specificity. This problem has been addressed previously.

For example, cell targeting has been achieved with adenovirus vectors by selective modification of the viral genome knob and fibre coding sequences to achieve expression of modified knob and fibre domains having specific interaction with unique cell surface receptors. Examples of such modifications are described in Wickham, et al (1997) J. Virol 71(11): 8221-8229 (incorporation of RGD peptides into adenoviral fibre proteins); Arnberg, et al (1997) Virology 227:239-244 (modification of adenoviral fibre genes to achieve tropism to the eye and genital tract); Harris and Lemoine (1996) TIG 12(10):400-405; Stevenson, et al (1997) J. Virol. 71(6): 4782-4790; Michael, et al (1995) Gene Therapy 2:660-668 (incorporation of gastrin releasing peptide fragment into adenovirus fibre protein); and Ohno, et al (1997) Nature Biotechnology 15:763-767 (incorporation of Protein A-IgG binding domain into Sindbis virus).

Other methods of cell specific targeting have been achieved by the conjugation of antibodies or antibody fragments to the envelope proteins (see, e.g. Michael, et al. (1993) J. Biol. Chem. 268:6866-6869, Watkins, et al. (1997) Gene Therapy 4:1004-1012; Douglas, et al. (1996) Nature Biotechnology 14: 1574-1578. Alternatively, particular moieties may be conjugated to the viral surface to achieve targeting (See, e.g. Nilson, et al. (1996) Gene Therapy 3:280-286 (conjugation of EGF to retroviral proteins). Additionally, cell specific targeting may be achieved by placing the virally encoded transgene under the control of a tissue specific promoter region allowing expression of the transgene preferentially in particular cell types.

BRIEF DESCRIPTION OF THE INVENTION

We provide an alternative approach to modify viral vectors to alter cell tropism.

Carbohydrates are highly stereospecific structures that play an important role in cellular trafficking. The reason for this is due to carbohydrates being able to form remarkably specific structures, which in turn has evolved cell receptors that only one or a limited few can interact with [8]. Glycosylation (i.e. addition of a sugar pendent group to a second molecule) of a protein or small molecule effectively allows it to gain entry to cells, which before would not have been accessible. We have employed mannose and galactose 2-imino-2-methoxyethyl-1-thiogylcosides, known to glycosylate selectively to primary amino groups found on lysine groups [9] to modify viral particles, in particular viral capsid proteins.

We show that increasing the level of glycosylation decreases infectivity of adenoviral particles since the number of lysine groups available for receptor and integrin binding is diminished. We also show that these modified viral particles can be specifically re-targeted to different cell-types.

According to an aspect of the invention there is provided a modified viral particle wherein the viral particle is engineered, either directly or indirectly, by the addition of at least one sugar pendent group.

"Engineered" means that the viral particle has been modified such that polypeptides comprising the virus have been modified by glycosylation to include at least one sugar pendent group and is to be distinguished from viral polypeptides that are naturally glycosylated. This does not exclude the modification of an existing glycosylated viral protein to alter its glycosylation state.

In a preferred embodiment of the invention said viral particle is modified by the addition of a sugar pendent group to at least one viral capsid polypeptide.

In a preferred embodiment of the invention said polypeptide is modified at a lysine amino acid residue.

In a preferred embodiment of the invention said viral particle is modified by the addition of at least one sugar selected from the group consisting of: mannose, galactose, n-acetyl glucosamine, n-acetyl neuraminic, acid n-glycolyl neuraminic acid, n-acetyl galactosamine, fucose, glucose, rhamnose, xylose, or a combinations of sugars, for example in an oligosacharide or scaffolded system.

Suitable carbohydrate moieties include monosaccharides, oligosaccharides and polysaccharides, and include any carbohydrate moiety that is present in naturally occurring glycoproteins or in biological systems. For example, optionally protected glycosyl or glycoside derivatives, for example optionally-protected glucosyl, glucoside, galactosyl or galactoside derivatives. Glycosyl and glycoside groups include both α and β groups. Suitable carbohydrate moieties include glucose, galactose, fucose, GlcNAc, GalNAc, sialic acid, and mannose, and oligosaccharides or polysaccharides comprising at least one glucose, galactose, fucose, GlcNAc, GalNAc, sialic acid, and/or mannose residue.

Any functional groups in the carbohydrate moiety may optionally be protected using protecting groups known in the art (see for example Greene et al, "Protecting groups in organic synthesis", 2nd Edition, Wiley, New York, 1991, the disclosure of which is hereby incorporated by reference). Suitable protecting groups for any —OH groups in the carbohydrate moiety include acetate (Ac), benzyl (Bn), silyl (for example tert-butyl dimethylsilyl (TBDMSi) and tert-butyldiphenylsilyl (TMDPSi)), acetals, ketals, and methoxymethyl (MOM). Any protecting groups may be removed before or after attachment of the carbohydrate moiety to the amino acid, peptide or protein.

In a preferred embodiment of the invention said sugars are unprotected.

Particularly preferred carbohydrate moieties include Glc$(Ac)_4$β-, Glc$(Bn)_4$β-, Gal$(Ac)_4$β-, Gal$(Bn)_4$β-, Glc$(Ac)_4$α(1,4)Glc$(Ac)_3$α(1,4)Glc$(Ac)_4$β-, β-Glc, β-Gal, -Et-β-GalEt-β-Glc, Et-α-Glc, -Et-α-Man, -Et-Lac, -β-Glc$(Ac)_2$, -β-Glc$(Ac)_3$, -Et-α-Glc$(Ac)_2$, -Et-α-Glc$(Ac)_3$, -Et-α-Glc$(Ac)_4$, -Et-β-Glc$(Ac)_2$, -Et-β-Glc$(Ac)_3$, -Et-β-Glc$(Ac)_4$, -Et-α-Man$(Ac)_3$, -Et-α-Man$(Ac)_4$, -Et-β-Gal$(Ac)_3$, -Et-β-Gal$(Ac)_4$, -Et-Lac$(Ac)_5$, -Et-Lac$(Ac)_6$, -Et-Lac$(Ac)_7$, and their deprotected equivalents.

Preferably, any saccharide units making up the carbohydrate moiety which are derived from naturally occurring sugars will each be in the naturally occurring enantiomeric form, which may be either the D-form (e.g. D-glucose or D-galactose), or the L-form (e.g. L-rhamnose or L-fucose). Any anomeric linkages may be α- or β-linkages.

It will be apparent that glycosylation of viral particles with various sugar pendent groups may be conducted by chemical or enzymatic means.

In a preferred embodiment of the invention at least 10% of the available sites in said viral particle are occupied by a sugar pendent group. Alternatively, at least 20%, 30%, 40%, 50%, 60%, 70%, 80%, 90%, 95% or 99% of the available sites in said viral particle are occupied by a sugar pendent group.

In a preferred embodiment of the invention said viral particle is a virus selected from the family groups consisting of: Adenoviridae; Alfamoviruses; Bromoviridae; Alphacryptoviruses; Partitiviridae; Baculoviridae; Badnaviruses; Betacryptoviruses; Partitiviridae; Bigeminiviruses; Geminiviridae; Birnaviridae; Bromoviruses; Bromoviridae; Bymoviruses; Potyviridae; Bunyaviridae; Caliciviridae; Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus Φ6 phage group; Cystoviridae; Cytorhabdoviruses; Rhabdoviridae; Group Carnation ringspot; Dianthovirus virus group; Group Broad bean wilt; Enamoviruse; Fabavirus virus group; Fijiviruses: Reoviridae; Filoviridae; Flaviviridae; Furovirus group; Group Geminivirus; Group Giardiavirus; Hepadnaviridae; Herpesviridae; Hordeivirus virus group; Hybrigeminiviruses: Geminivirida; Idaeoviruses; Ilarvirus virus group; Inoviridae; Ipomoviruses: Potyviridae; Iridoviridae; Levivridae; Lipothrixviridae; Luteovirus group; Machlomoviruses; Macluraviruses; Marafivirus virus group; Maize chlorotic dwarf virus group; icroviridae; Monogeminiviruses: Geminiviridae; Myoviridae; Nanaviruses; Necrovirus group; Nepovirus virus group; Nodaviridae; Nucleorhabdoviruses: Rhabdoviridae; Orthomyxoviridae; Oryzaviruses: Reoviridae; Ourmiaviruses; Papovaviridae; Paramyxoviridae; Parsnip yellow fleck virus group; Partitiviridae; Parvoviridae including adeno-associated viruses; Pea enation mosaic virus group; Phycodnaviridae; Phytoreoviruses: Reoviridae; Picornaviridae; Plasmarviridae; Podoviridae; Polydnaviridae; Potexvirus group; Potyvirus; Poxyiridae; Reoviridae; Retroviridae; Rhabdoviridae; Group Rhizidiovirus; Rymoviruses: Potyviridae; Satellite RNAs; Satelliviruses; Sequiviruses: Sequiviridae; Sobemoviruses; Siphoviridae; Sobemovirus group; SSVI-Type Phages; Tectiviridae; Tenuivirus; Tetravirirdae; Group Tobamovirus; Group Tobravirus; Togaviridae; Group Tombusvirus; Tospoviruses: Bunyaviridae; Group Torovirus; Totiviridae; Tymoviruses; Group Tymovirus; Plant virus satellites; Umbraviruses; Unassigned potyviruses: Potyviridae; Unassigned rhabdoviruses; Rhabdoviridae; Varicosaviruses; Waikaviruses: Sequiviridae; and Ungrouped viruses.

In a preferred embodiment of the invention said viral particle is a virus selected from the family groups consisting of: Baculoviridiae, Parvoviridiae, Picornoviridiae, Herpesveridiae, Poxyiridae, Adenoviridiae, or Picornnaviridiae.

In a preferred embodiment of the invention said viral particle is of the Adenoviridiae family. Preferably said viral particle is of the genus *Mastadenovirus*. Preferably said viral particle is a type 2 or type 5 adenovirus.

In a preferred embodiment of the invention said capsid protein is selected from the group consisting of: hexon protein, penton base protein or fibre protein, including the knob domain of fibre protein.

The invention has application to all capsid polypeptides. The hexon polypeptide includes peripentonal hexon and hexon associate d proteins. The penton polypeptide include penton base and fibre. These polypeptides are also associated with stabilising proteins v11, iiia, ix, v111 and triplexes (See W. Chiu, J. F. Rixon, Virus Research 2002, vol 82 9-17, which is incorporated by reference). All icosahedral capsid proteins are generalised as hexameric and pentameric. Within the scope of the invention are capsid proteins from non-icosahedral viruses, for example ms2 proteins of bacteriophage.

A number of viruses are commonly used as vectors for the delivery of exogenous genes. Commonly employed vectors include recombinantly modified enveloped or non-enveloped DNA and RNA viruses, preferably selected from baculoviridiae, parvoviridiae, picornoviridiae, herpesveridiae, poxviridae, adenoviridiae, or picornnaviridiae. Chimeric vectors may also be employed which exploit advantageous elements of each of the parent vector properties (See e.g., Feng, et al (1997) Nature Biotechnology 15:866-870). Such viral vectors may be wildtype or modified by recombinant DNA techniques to be replication deficient, conditionally replicating or replication competent. Preferred vectors are derived from the adenoviral, adeno-associated viral and retroviral genomes.

In preferred practice of the invention, the vectors are derived from the human adenovirus genome.

Particularly preferred vectors are derived from the human adenovirus serotypes 2 or 5. The replicative capacity of such vectors may be attenuated (to the point of being considered "replication deficient") by modifications or deletions in the E1a and/or E1b coding regions. Other modifications to the viral genome to achieve particular expression characteristics or permit repeat administration or lower immune response are preferred.

Alternatively, the viral vectors may be conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342-343; Russell, and S. J. (1994) Eur. J. of Cancer 30A(8): 1165-1171. Additional examples of selectively replicating vectors include those vectors wherein an gene essential for replication of the virus is under control of a promoter which is active only in a particular cell type or cell state such that in the absence of expression of such gene, the virus will not replicate. Examples of such vectors are described in Henderson, et al., U.S. Pat. No. 5,698,443 and Henderson, et al., U.S. Pat. No. 5,871,726, which are herein incorporated by reference in their entirety.

Additionally, the viral genome may be modified to include inducible promoters that achieve replication or expression only under certain conditions. Examples of inducible promoters are known in the scientific literature (See, e.g. Yoshida and Hamada (1997) Biochem. Biophys. Res. Comm. 230:426-430; Iida, et al. (1996) J. Virol. 70(9):6054-6059; Hwang, et al. (1997) J. Virol 71(9):7128-7131; Lee, et al. (1997) Mol. Cell. Biol. 17(9):5097-5105; and Dreher, et al. (1997) J. Biol. Chem. 272(46); 29364-29371.

The viruses may also be designed to be selectively replicating viruses. Particularly preferred selectively replicating viruses are described in Ramachandra, et al WO00/22137 and Howe, J. WO WO0022136 that are incorporated by reference.

It has been demonstrated that viruses that are attenuated for replication are also useful. For example the adenovirus dl1520 containing a specific deletion in the E1b55K gene (Barker and Berk (1987) Virology 156: 107) has been used with therapeutic effect in human beings. Such vectors are also described in McCormick U.S. Pat. No. 5,677,178 and McCormick, U.S. Pat. No. 5,846,945. The present invention may also be used in combination with the administration of such vectors to minimize the pre-existing or induced humoral immune response to such vectors.

In a preferred embodiment of the invention the viral genome is modified by the inclusion of at least one heterologous nucleic acid molecule. Preferably said viral genome is an adenoviral genome.

In a further preferred embodiment the genome of the virus is adapted for eukaryotic expression of said heterologous nucleic acid molecule.

Typically said adaptation includes, by example and not by way of limitation, the provision of transcription control sequences (promoter sequences) that mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis-acting nucleic acid sequences often found 5' to the transcription initiation site of a gene (enhancers can also be found 3' to a gene sequence or even located in intronic sequences and are therefore position-independent). Enhancers function to increase the rate of transcription of the gene to which the enhancer is linked. Enhancer activity is responsive to trans-acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues.

Promoter elements also include so-called TATA box and RNA polymerase initiation selection sequences which function to select a site of transcription initiation. These sequences also bind polypeptides that function, inter alia, to facilitate transcription initiation selection by RNA polymerase.

Adaptations that facilitate the expression of viral-encoded genes include the provision of transcription termination/polyadenylation sequences. This also includes the provision of internal ribosome entry sites (IRES) that function to maximise expression of viral-encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc (1994).

The specificity and safety of gene therapy is enhanced by limiting the expression of the gene in specific tissues and/or cells. Preferably, therefore the expression of the heterologous nucleic acid is controlled by a tissue and/or cell specific and/or cancer specific promoter.

In a further preferred embodiment of the invention the heterologous nucleic acid molecule encodes a therapeutic agent.

The heterologous nucleic acid molecule may encode tumour suppressor genes, antigenic genes, cytotoxic genes, cytostatic genes, pro-drug activating genes, apoptotic genes, pharmaceutical genes or anti-angiogenic genes.

Preferably the therapeutic agent is a polypeptide.

Preferably the heterologous nucleic acid encodes an antigenic polypeptide. In order to facilitate immune recognition, parts of the antigenic polypeptide or sequences representing antigenic epitopes may be expressed either alone or fused to those of other antigens. Selected antigens may be presented by MHC class I and MHC class II molecules, as well as by non-classical MHC molecules. Preferably, the antigenic polypeptide is derived from a tumour cell-specific antigen, ideally a tumour rejection antigen. Tumour rejection antigens are well known in the art and include, by example and not by way of limitation, the MAGE, BAGE, GAGE and DAGE families of tumour rejection antigens, see Schulz et al Proc Natl Acad Sci USA, 1991, 88, pp 991-993.

It has been known for many years that tumour cells produce a number of tumour cell-specific antigens, some of which are presented at the tumour cell surface. These are generally referred to as tumour rejection antigens and are derived from larger polypeptides referred to as tumour rejection antigen precursors. Tumour rejection antigens are presented via HLA class I or class II molecules to the host's T cells. Other tumour-specific antigens may be presented by CD1 molecules or may directly activate certain cells of the immune system, e.g NK or NKT cells. Examples for the latter are MHC-like tumour-specific stress molecules, such as MICA-MICE. In general, the immune system recognises these abnormally expressed molecules as foreign or abnormal and destroys cells expressing these antigens. If a transformed cell escapes detection and becomes established, a tumour develops. Various vaccines have been developed based on dominant tumour rejection antigens to provide individuals with a preformed defence to the establishment of a tumour.

In a preferred embodiment of the invention the therapeutic agent is a tumour rejection antigen.

In a still further preferred embodiment of the invention said heterologous nucleic acid encodes a cytotoxic agent. Said cytotoxic agent may be pseudomonas exotoxin; ricin toxin; or diptheria toxin and the like.

In a further preferred embodiment of the invention said heterologous nucleic acid encodes a polypeptide with cytostatic activity thereby inducing cell-cycle arrest.

Examples of such cytostatic genes include p21, the retinoblastoma gene, the E2F-Rb gene, genes encoding cyclin dependent kinase inhibitors such as P16, p15, p18 and p19, the growth arrest specific homeobox (GAX) gene as described in Branellec, et al. (see WO97/1645 and WO96/30385).

In a still further preferred embodiment of the invention said heterologous nucleic acid encodes a pharmaceutically active polypeptide.

Preferably said pharmaceutically active polypeptide is a cytokine. The term "cytokine gene" refers to a nucleotide sequence, the expression of which in a cell produces a cytokine. Examples of such cytokines include GM-CSF, the interleukins, especially IL-1, IL-2, IL-4, IL-5, IL-12, IL-10, IL-15, IL-19, IL-20, interferons of the α, β and γ subtypes, and members of the tumour necrosis factor family.

In a further preferred embodiment of the invention said pharmaceutically active polypeptide is a chemokine.

The term "chemokine gene" refers to a nucleotide sequence, the expression of which in a cell produces a chemokine. The term chemokine refers to a group of structurally related low-molecular weight cytokines secreted by cells having mitogenic, chemotactic or inflammatory activities. They are primarily cationic proteins of 70 to 100 amino acid residues that share four conserved cysteines. These proteins can be sorted into two groups based on the spacing of the two amino-terminal cysteines. In the first group, the two cysteines are separated by a single residue (C-x-C), while in the second group, they are adjacent (C—C). Examples of member of the 'C-x-C' chemokines include but are not limited to platelet factor 4 (PF4), platelet basic protein (PBP), interleukin-8 (IL-8), IP-10, melanoma growth stimulatory activity protein (MGSA), BCA-1, I-TAC, SDF-1 etc. and pre-B cell growth stimulating factor (PBSF). Examples of members of the 'C—C' group include but are not limited to monocyte chemotactic protein 1 (MCP-1), MCP-2, MCP-3, MCP-4, macrophage inflammatory protein 1 α (MIP-1-α), MIP-1-β, MIP3α, MIP3β, MIP-5/HCC-2, RANTES, thymus and activation-regulated chemokine (TARC), eotaxin, I-309, human protein HCC-1 and HCC-3.

In a still further preferred embodiment of the invention said polypeptide is an antibody or active binding fragment thereof. Preferably said antibody or binding fragment is a monoclonal antibody. Preferably said fragment is a Fab fragment or a single chain antibody variable fragment or a "domain antibody".

Domain antibodies are the smallest binding part of an antibody (approximately 13 kDa). Examples of this technology is disclosed in U.S. Pat. No. 6,248,516, U.S. Pat. No. 6,291,158, U.S. Pat. No. 6,127,197 and EP0368684 which are all incorporated by reference in their entirety.

In a further preferred embodiment of the invention said antibody is a humanised or chimeric antibody.

A chimeric antibody is produced by recombinant methods to contain the variable region of an antibody with an invariant or constant region of a human antibody. A humanised antibody is produced by recombinant methods to combine the complementarity determining regions (CDRs) of an antibody with both the constant (C) regions and the framework regions from the variable (V) regions of a human antibody.

Chimeric antibodies are recombinant antibodies in which all of the V-regions of a mouse or rat antibody are combined with human antibody C-regions. Humanised antibodies are recombinant hybrid antibodies that fuse the complementarity determining regions from a rodent antibody V-region with the framework regions from the human antibody V-regions. The C-regions from the human antibody are also used. The complimentarily determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

In a further preferred embodiment of the invention said heterologous nucleic acid encodes a tumour suppressor polypeptide. Preferably said tumour suppressor polypeptide is p53.

A tumour suppressor gene is a gene encoding a protein that suppresses tumour formation, thus it is a gene that normally prevents unlimited cell division. When both copies of the gene are lost or mutated the cell is transformed to a cancerous phenotype. Examples are the p53, retinoblastoma and Wilm's tumour genes.

In a further preferred embodiment of the invention said heterologous nucleic acid encodes a polypeptide that induces apoptosis or other forms of cell death.

Examples of pro-apoptotic genes include p53, the adenovirus E4orf4 gene, p53 pathway genes, genes encoding caspases or proapoptotic Bcl-2 family members, proapoptotic ligands (TNF, FasL, TRAIL) and/or their receptors (TNFR, Fas, TRAIL-R1, TRAIL-R2).

A cytolytic function has also been ascribed to the E3/11.6K (10.5 K) protein of subgenus C adenoviruses that may therefore be incorporated as a therapeutic gene.

In a further preferred embodiment of the invention the polypeptide is a pro-drug activating polypeptide.

The term "pro-drug activating genes" refers to nucleotide sequences, the expression of which, results in the production of proteins capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5 fluorouracil, a potent antitumour agent. The lysis of the tumour cell provides a localized burst of cytosine deaminase capable of converting 5FC to 5FU at the localized point of the tumour resulting in the killing of many surrounding tumour cells. This results in the killing of a large number of tumour cells without the necessity of infecting these cells with an adenovirus (the so-called bystander effect). Similarly the *Escherichia coli* nitroreductase gene can be expressed in situ to produce nitroreductase enzyme that activates harmless prodrugs (eg CB 1954) to potent alkylating species. Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product become susceptible to selective killing by the administration of ganciclovir may be employed.

In a further preferred embodiment of the invention the polypeptide has anti-angiogenic activity.

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in PNAS (USA) (1998) 95:8795-8800), endostatin and including antibodies and antibody fragments that bind pro-apoptotic proteins to block their activity.

In a further preferred embodiment of the invention the therapeutic molecule is an antisense nucleic acid molecule.

Antisense technology is a way to target the RNA molecules rather than the proteins that they encode. Antisense technology does not rely on small molecule therapeutics to target RNA targets, but instead employs modified strands of DNA that can bind to specific RNA sequences. When the modified DNA strands bind to the targeted RNA, the RNA can no longer be translated into protein. As a result, if a disease is characterized by the excessive production of a particular protein product, targeting the RNA which encodes the protein and preventing their translation may be a safer, more viable, and more effective form of treatment.

In a further preferred embodiment of the invention the therapeutic molecule is an inhibitory RNA (iRNA), also known as short interfering (siRNA).

iRNA molecules are RNA molecules that function to bind to specific cellular target molecules, thereby inducing the specific degradation of the targeted mRNA. As a consequence the synthesis of specific proteins is greatly diminished. This therefore allows the specific elimination of expression of certain genes. Systems for both transient and permanent expression of iRNA have been developed which may be incorporated into the modified virus of the invention. Typically, iRNA's are small double stranded RNA molecules that vary in length from between 10-100 base pairs in length although large siRNA's e.g. 100-1000 bp can be utilised. Preferably the siRNA's are about 21 base pairs in length.

Typically, when using adenovirus-based vectors for gene therapy, the virus has to be modified to eliminate or minimise the disease-causing potential by rendering the virus replication-deficient. Typically, such a modification involves the deletion of the E1 region genes. Thus, in a further preferred embodiment of the invention the said adenovirus is made replication-deficient, preferably the adenovirus is E1 negative.

In addition, the adenovirus virus vector may harbour deletions within the E3 region or may be deficient in one or more E3 functions. Moreover, certain E3 genes, individual or as a whole, may be replaced by other "therapeutic" genes, including genes encoding antigenic proteins for vaccination If a protein is being utilised for therapeutic purposes it is often desirable to be able to confirm and visualise its expression. This is typically achieved by the use of protein tags. The DNA sequence that codes for the therapeutic protein is tagged by fusing it to the sequence of another protein that can be easily detected. When the organism expresses the therapeutic protein, the protein "tags" are also produced.

Proteinaceous fluorophores are known in the art. Green fluorescent protein, GFP, is a spontaneously fluorescent protein isolated from coelenterates, such as the Pacific jellyfish, *Aequoria victoria*. Its role is to transduce, by energy transfer, the blue chemiluminescence of another protein, aequorin, into green fluorescent light. GFP can function as a protein tag, as it tolerates N- and C-terminal fusions to a broad variety of proteins many of which have been shown to retain native function. Other proteinaceous fluorophores include yellow, red and blue fluorescent proteins.

In a further preferred embodiment of the invention the modified viral particle according to the invention further comprises a protein tag. Preferably the protein tag is a fluorescent protein. Even more preferably the fluorescent protein is green fluorescent protein.

In a still further preferred embodiment of the invention the viral genome sequence is modified to encode green fluorescent protein, a derivative thereof or another fluorescent protein.

The fluorescent proteins may be expressed independently from other viral proteins or heterologous sequences using specific promoters, enhancers and polyadenylation signals, as discussed above. Other marker proteins, such as β-galacosidase, may be expressed in the viral genome to quantitate the efficiency of transduction/infection.

It will be readily apparent to those of skill in the art that there may be modifications and/or deletions to the above referenced heterologous nucleic acid molecules so as to encode functional sub-fragments of the wild type protein which may be readily adapted for use in the practice of the present invention. For example, the reference to the p53 gene includes not only the wild type protein but also modified p53 proteins. Examples of such modified p53 proteins include modifications to p53 to increase nuclear retention, such as the deletion of the calpain consensus cleavage site (Kubbutat and Vousden (1997) Mol. Cell. Biol. 17:460-468, modifications to the oligomerization domains (as described in Bracco, et al WO97/0492 or U.S. Pat. No. 5,573,925).

It will be readily apparent to those of skill in the art that the above therapeutic genes may be localized to particular intracellular locations by inclusion of a targeting moiety, such as a signal peptide, an endoplasmic reticulum retention signal, other transport motifs or a nuclear localization signal (NLS). In other instances, targeting signals may be included that allow efficient secretion of the therapeutic gene.

According to a further aspect of the invention there is provided a pharmaceutical composition comprising a modified virus according to the invention.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents, such as chemotherapeutic agents.

The viral compositions of the invention can be administered by any conventional route, including injection or by gradual infusion over time. The administration may, for example, be oral, intravenous, intraperitoneal, intramuscular, intracavity, subcutaneous, or transdermal.

The compositions of the invention are administered in effective amounts. An "effective amount" is that amount of a composition that alone, or together with further doses, produces the desired response. In the case of treating a particular disease, such as cancer, the desired response is inhibiting the progression of the disease. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

The compositions used in the foregoing methods preferably are sterile and contain an effective amount of virus for producing the desired response in a unit of weight or volume suitable for administration to a patient. The response can, for example, be measured by measuring the physiological effects of the viral composition, such as regression of a tumour, decrease of disease symptoms, modulation of apoptosis, etc. Other assays will be known to one of ordinary skill in the art and can be employed for measuring the level of the response.

The doses of virus administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of virus are formulated and administered in doses between 1 ng and 0.1 mg and generally will be formulated and administered according to standard procedures. Other protocols for the administration of viral compositions will be known to one of ordinary skill in the art, in which the dose amount, schedule of injections, sites of injections, mode of administration (e.g., intra-tumoural) and the like vary from the foregoing.

The administration of viral compositions to mammals, other than humans (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the pharmaceutical viral compositions of the invention are applied in pharmaceutically acceptable amounts and in pharmaceutically acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

Viral compositions may be combined, if desired, with a pharmaceutically acceptable carrier. The term "pharmaceutically-acceptable carrier" as used herein means one or more compatible solid or liquid fillers, diluents or encapsulating substances that are suitable for administration into a human. The term "carrier" denotes an organic or inorganic ingredient, natural or synthetic, with which the active ingredient is combined to facilitate the application. The viral pharmaceutical compositions may contain suitable buffering agents, including: acetic acid in a salt; citric acid in a salt; boric acid in a salt; and phosphoric acid in a salt. The viral pharmaceutical compositions also may contain, optionally, suitable preservatives, such as: benzalkonium chloride; chlorobutanol; parabens and thimerosal.

Compositions suitable for parenteral administration conveniently comprise a sterile aqueous or non-aqueous preparation of viral particles, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided a method of treatment of a subject comprising administering to a subject a therapeutically effective amount of a modified virus according to the invention.

In a preferred method of the invention said subject is human.

In a preferred method of the invention said viral particle includes a viral genome that comprises a nucleic acid molecule that encodes a therapeutic polypeptide.

In a preferred method of the invention said viral particle includes a nucleic acid molecule that encodes a therapeutic polypeptide that replaces a non-functional gene product.

In a preferred method of the invention said treatment is the treatment of cancer.

According to a further aspect of the invention there is provided a method to modify a viral particle comprising the steps of:

i) forming a preparation comprising a viral particle and at least one sugar donating agent;
ii) incubating the preparation formed in (i) under conditions conducive to the modification of the viral particle with a sugar.

In a preferred method of the invention said viral particle is an adenoviral particle.

In a further preferred method of the invention said sugar donating agent is a 2-imino-2-methoxyethyl-1-thioglycoside.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE FIGURES

An embodiment of the invention will now be described by example only and with reference to the following figures.

MATERIALS AND METHODS

Figure 1:
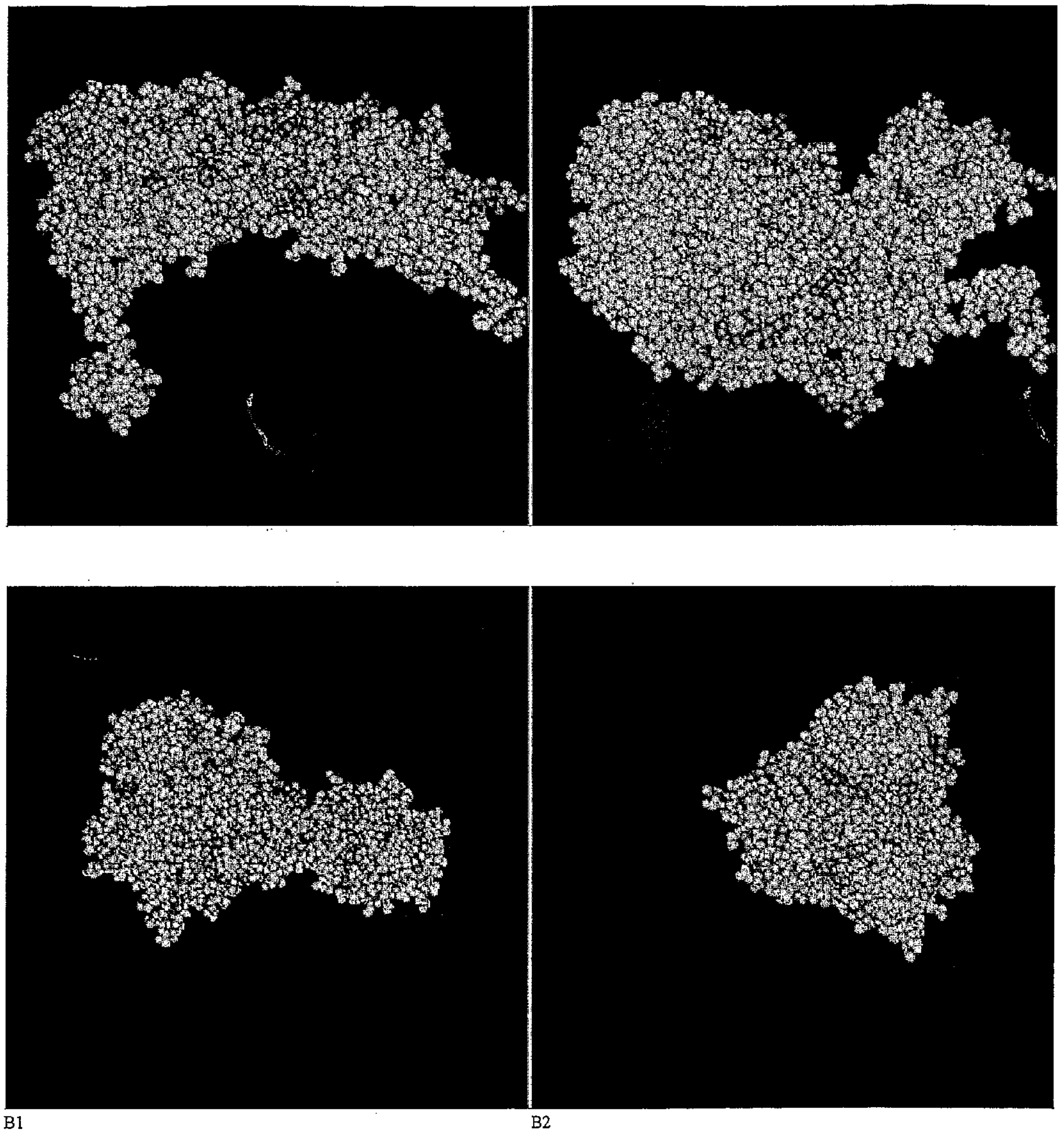
FIG. 1 illustrates the X-ray structure of Hexon and Fibre monomers reveal position and number of lysine groups in red. A1=Hexon monomer equatorial plain, A2=Hexon monomer axial plane, B1=Fibre monomer equatorial plain, B2=Fibre monomer axial plain. Fibre proteins combine to form the knob domain at the end of each fibre.

Synthesis of 2-imino-2-methoxyethyl-1-thiogylcosides (scheme 2) is known in the art [11].

Control Samples

Control samples of adenovirus were treated in the same way as modified, replacing the volume of reactive IME with the same volume of PBS 7.4.

Purification of Viral Samples

Viral samples were purified using Microspin S-400HR columns and centrifuged (2 min, 2600 rpm).

Picogreen Analysis

DNA Standard Preparation

A 1 ng/ml (TE as buffer) Lambda DNA solution was made and serially diluted to give 0.5, 0.25, 0.125, 0.0625, 0.03 ng/ml and a TE blank. These solutions (100 ul of each) were added to a 96 black well plate to give 7 standard wells. Picogreen (100 ul of X40 dilution) was added to each and analysed using a victor plate reader (Fluorescein 1.0 min)

Sample Preparation (on Disassociated Virus)

5 ul of virus was deactivated in a water bath (56° C., 30 min) and diluted with 95 ul of TE 5% SDS solution. 10 ul of this solution was added to 90 ul of TE in a well on a 96 black well plate. Picogreen (100 ul of X40 dilution) was added to each and analysed using a victor plate reader (Fluorescein 485/515.0 min).

Sample Preparation (on Whole Virus)

5 ul of virus was deactivated in a water bath (56° C., 30 min) and diluted with 95 ul of TE solution. 10 ul of this solution was added to 90 ul of TE in a well on a 96 black well plate. Picogreen (100 ul of X40 dilution) was added to each and analysed using a victor plate reader (Fluorescein 485/515.0 min).

All samples and standards were loaded onto the plate before addition of Picogreen reagent. Picogreen reagent is photon sensitive and therefore should be added to every sample/standard at the same time and within a short time of analysis.

Glycosylation of Adenovirus with 2-Imino-2-methoxyethyl-D-thioglycopyranoside

2-S-(2,3,4,6-tetra-O-acetyl-D-glycopyranosyl)-2-thiocyanomethyl (100 mg) was dissolved in anhydrous methanol (2.3 ml). To this solution a methanolic solution of sodium methoxide was added (5.2 mL, 0.01 M) and stirred at R.T under dry $N_2$(g) for 36-48 hrs. The solution was evaporated to dryness at <30° C. (either as a white gum or a clear oil (both phases used with comparable (results). 2-imino-2-methoxyethyl-1-thiomannose was dissolved (vortex aided) in PBS 7.4 (100 ul) to form a saturated solution and 5 ul of this solution immediately added and mixed by pipette to a fresh sample of adenovirus type 5 (45 ul) (reagent excess estimated at 5.8E+3 sugar units per virus lysine group). The reagent solution was further diluted by 5 ml and then 10 ml each time taking 5 ul and mixing to a fresh solution of adenovirus (45 ul, 5.72E+11 viral particles $ml^{-1}$). To give an equivalent reagent excess of 5.8E±2 and 2.9E±2 respectively per primary amino group on the virus capsid. Each sample was shaken (without vortex) and left at room temp for 4 hrs before storing at 4° C. (purified within 16 hrs used for transfection within 48 hrs, unless stored at −80° C. in storage buffer until needed).

HPLC Analysis

Sample volumes injected varied from 5-15 ul. Samples presented represent the equivalent of 6E+8 virus particles. Samples were run on a KromaSystem 2000, matrix=100% PBS 7.4, total flow=1 mL/min, a sepharose column. Wavelengths monitored specifically=210, 260, 282 and 410 nm.

Electrode Buffer:

Tris (9 g), Glycine (43.2 g), SDS (3 g) in 600 ml water. (store at 4° C.). (X5 dilution).

10% Separating Gel:

(add in this order) DI water (4.045 ml), 1.5M Tris (2.5 ml), 10% SDS (100 ul), Acrylamide (3.3 ml), 10% Ammonium persulphate (50 ul), TEMED (15 ul).

6% Separating Gel:

Vary the ratio of water/Acrylamide accordingly. Other reagent volumes remain the same.

Stacking Gel:

(add in this order) DI water (6.1 ml), 0.5M Tris (2.5 ml), 10% SDS (100 ul), Acrylamide (1.33 ml), 10% Ammonium persulphate (50 ul), TEMED (15 ul).

Silver Stain

Solutions

1. Fixer(aq)
   a. 10% acetic acid
   b. 40% Methanol
2. Wash 1
   a. 100% DI water KromaSystem 2000 Version 1.83 PROGRAM FILE LISTING

| Time | Device | Function | <<Parameter1>> | <<Parameter2>> | <<Parameter3>> |
|---|---|---|---|---|---|
| 0.05 | | Flow | Total Value: 1.000 | Step | |
| 0.30 | DAD 440 | | Sampling time: 40 | | |
| 0.45 | DAD 440 | Spec Range | low lim.: 190 | up lim.: 800 | bunching: 10 |
| 0.50 | DAD 440 | Scan/sec | scan/sec: 1.04 | | |
| 0.60 | DAD 440 | Response | sec: 0.800 | | |
| 0.70 | DAD 440 | Chromatog. | channel: 4 | wavelen.: 210 | bandwid.: 10 |
| 0.80 | DAD 440 | Chromatog. | channel: 5 | wavelen.: 260 | bandwid.: 10 |
| 0.90 | DAD 440 | Chromatog. | channel: 6 | wavelen.: 282 | bandwid.: 10 |
| 1.00 | DAD 440 | Chromatog. | channel: 7 | wavelen.: 410 | bandwid.: 10 |
| 1.10 | DAD 440 | Acq. Ready | | | |
| 1.20 | AS 465 | Wash | | | |
| 1.20 | SFM 25 | Excitation L | Excit: 590 | | |
| 1.30 | SFM 25 | Emission L | Emiss: 616 | | |
| 1.40 | SFM 25 | Hi Voltage | Hi Volt: 800 | | |
| 2.20 | AS 465 | Inject | | | |
| 2.25 | | Acquis. On | Channel: 24567S | Average: ON | Step: |
| 2.30 | SFM 25 | Autozero | | | |
| 2.35 | DAD 440 | Autozero | channel: A | | |
| 50.00 | | Acquis. Off | | | |
| 50.10 | | End | | | |

SDS-PAGE Gel

Invitrogen NuPAGE™ 4-12% BIS-TRIS gel 1.0 mm×15 well pre-cast gels were used to separate viral proteins. Between 2-10 ng of protein was loaded onto each gel in NuPAGE™ LDS sample buffer.

Buffers

Separating Gel Buffer (1.5 M Tris HCl):

Tris base (27.23 g) dissolved in 80 ml DI water and pH adjusted to 8.8 with conc. HCl. Make up to 150 ml with DI Water (store at 4° C.).

Stacking Gel Buffer (0.5M Tris HCl):

Tris base (6 g) dissolved in 60 ml DI water and pH adjusted to 6.8 with conc. HCl. Solution made up to 100 ml with DI water (store at 4° C.).

10% SDS:

Sodium-dodecyl-sulphate (log) dissolved in DI water (90 ml) and with stirring made up to 100 ml (store at r.t).

Sample Buffer 1:

DI water (3.8 ml), 0.5M Tris (1 ml), Glycerol (0.8 ml), 10% SDS (1.6 ml), 2-mercaptoethanol (0.4 ml), 1% Bromophenol blue (0.4 ml) (store at r.t).

3. Wash 2 (aq)
   a. 20% Ethanol
4. Sensitizer(aq)
   a. 12.5% Gluteraldehyde
5. Stain (make up in this order, use immediately after preparation for best results)
   a. 20% Silver Nitrate(aq) (1 ml)
   b. 25% Ammonia Hydroxide(aq) (1 ml)
   c. 5% Sodium Hydroxide (5 ml)
   d. 20% Ethanol(aq) (93 ml)
6. Developer
   a. 20% Ethanol(aq) (100 ml)
   b. 37% Formaldehyde (100 ul)
   c. 2.3M Citric acid (25 ul)
7. Preserver(aq)
   a. 5% Glycerol
   b. 10% Acetic acid Sequence 1. Fixer (5 min)
2. Wash 1 (5 min)
3. Sensitizer (7.5 min)
4. Wash 1 (2×5 min)

5. Wash 2 (5 min) Transfer to new container
6. Stain (15 min)
7. Wash 2 (5 min) Transfer to new container
8. Wash 2 (5 min)
9. Developer (watch for bands and remove when necessary)
10. Preserver Coomassie Brilliant Blue Stain SDS PAGE gel was soaked in Coomassie blue reagent (50 ml) for 12 hrs (or until bands were seen) with agitation. Gel was destained with destaining solution until only blue bands remained.

Periodic Acid/Pro Emerald 488 stain

Glycoprotein stain kit was purchased from Molecular probes [7] and used according to supplied protocol.

Transfection of A549 Cell

Bovine lung carcinoma cells, previously isolated, were grown from cell lines in Dulbecco's Modification of Eagle's Medium (DMEM), 10% foetal calf serum (FCS) and plated onto a flat bottom 96 well plate (1E+4 cells/well and left overnight to adhere. DMEM was removed and cells washed once with Dubelcco's PBS (without Ca & Mg). Transfection media (virus in 200 uL DMEM) was added and cells incubated for 30-45 mins. Transfection media removed and cells washed with Dubelcco's PBS (without Ca & Mg) (3×200 uL). Cells incubated in DMEM for min 12 hrs before analysing by luminometry.

Cell Isolation

Monocytes (Mo) and lymphocytes were isolated from anticogulated human peripheral blood according to the methods of Graziani-Bowering et al[8]. Human endothelial cells were isolated from saphenous vein by filling the vessel with 0.2% warmed collagenase solution (Sigma Blend C8051) and Incubating at 37 for 20 minutes. One end of the vessel was anchored and the vein was with surgical scissors. Endothelial cells were removed Using a cell scraper. The tissue was rinsed with endothelial growth medium (EGM (Endothelial Growth medium-2 Bulletkit (EGM-2, Biowhittaker clonetics CC3162)) and the suspended cells were centifuged for 10 minutes at 400 g and room temperature. The pelleted cells were resuspend in EGM and cultured at 37 in 5% Co2 incubator in 2% gelatin (Sigma G1393) coated flasks until the endothelial cells become confluent.

Cell Culture and Pre-Treatment

Lymphocytes and monocytes were maintained in RPMI media (RPMI (Sigma, UK), 10% fetal bovine serum (Life Technologies, UK), 2 mM glutamine, 100 units/ml penicillin and 0.1 mg/ml streptomycin (Sigma, UK)). Endothelial cells were cultured as described above.

Monocytes were treated with 100 ng/ml M-CSF (R & D systems) for 3 days prior to transfection.

Lymphocytes were treated with 1 ng/ml PMA (Sigma, UK) for 24 hours prior to adenovirus transfection.

Transfection 2.5×105 cells per well in 0.7 ml volume (lymphocytes & monocytes) were plated into wells of Falcon 8 well glass culture slide (code 354118) and allowed to adhere. (EC were plated and grown in slide). Adherent cells were washed 3 times in un-supplemented RPMI prior to transfection.

Cells were transfected with adenovirus at an MOI of 500. Cells were transfected with GFP virus, GFP-mann, GFP-gal or media alone. Virus was diluted in serum free RPMI (but containing antibiotic and glutamine etc) and 200 μl of each preparation or media control was added to the cells. Cells were transfected with adenovirus in serum free conditions for 2 hours then 5001 of serum containing media was added. Cells were incubated for 72 hours and percentage of cells transfected was determined by counting under fluorescent illumination (using GFP filter) to determine the percentage, which were expressing GFP protein.

Additional Experimental

Synthesis of 2-imino-2-methoxyethyl-1-thioglycosides

Synthesis of 1,2,3,4,6-penta-O-acetyl-β-D-galactopyranose

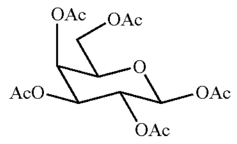 [SMILES: CC(=O)OCC1OC(OC(C)=O)C(OC(C)=O)C(OC(C)=O)C1OC(C)=O]

To galactose (50 g, 0.128 mol), slurried in Acetic Anhydride (200 mL, 1.96 mol) a warm solution of Iodine (2.5 g) in Acetic anhydride (10 mL) was charged in portions (exothermic). Batch cooled in an ice-bath until exothermic reaction was completed. (TLC, Silica, 1:1 Petrol/EtOAc, product Rf: 0.47). Product extracted with DCM/10% sodium thiosulphate (1:1, 1 L). Organic layer quenched with a saturated solution of Sodium Bicarbonate. Organic layer dried with a saturated solution of brine (3×200 ml) and magnesium sulphate. Batch evaporated to dryness under vacuum to afford yellow/orange oil (106 g, 98.6%). $[\alpha]_D^{22}$+23.4 ($CHCl_3$, C=1.0) (Lit[1]+22). $^1$H NMR (CDCl3, 400 MHz) δ=1.95, 1.99, 2.09, 2.15, 2.20 (sx5, 3Hx5, —C(O)$CH_3$x5), 4.04-4.22 (m, 2H, H6, H6[1]), 4.3-4.4 (m, 1H, H-5) 5.1 (dd, $J_{2,3}$10.3 Hz, $J_{3,4}$3.5 Hz, 1H, H-3), 5.3 (dd, $J_{1,2}$8.8 Hz, $J_{2,3}$9.8 Hz, 1H, H-2), 5.4 (br, d, $J_{3,4}$3.3 Hz, 1H, H-4), 5.72 (d, $J_{1,2}$8.3 Hz, 1H, H-1).

Synthesis of 2,3,4,6-tetra-O-acetyl-α-D-galactopyranosyl bromide

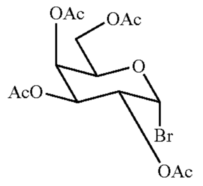 [SMILES: CC(=O)OCC1OC(Br)C(OC(C)=O)C(OC(C)=O)C1OC(C)=O]

12,3,4,6-penta-O-acetyl-β-D-galactopyranose (35 g) dissolved in HBr (33% in AcOH, 190 ml) with DCM (80 ml) as solvent aid. Reaction followed by TLC (Petrol:EtOAc 1:1) which showed reaction completion (Rf's: Starting material (0.46), product (multiple peaks, key peak at 0.69, multiple peaks possibly due to compound instability on silica and or hydrolysis by-products). Reaction mixture quenched with distilled water (IL) followed by immediate extraction with DCM (3×250 ml). Organic layer neutralised with a saturated solution of Sodium Bicarbonate (2×1 L). Finally, organic layer dried with sodium sulphate and evaporated (maintaining the temperature<30° c.) to dryness under vacuum to afford a brown oil (37.5 g, quantitative yield). $[\alpha]_D^{22}$+212 ($CHCl_3$, C=1.0) (Lit[2]+210). $^1$H NMR (CDCl3, 400 MHz). δ=2.01, 2.05, 2.10, 2.15 (sx4, 3H x4, —C(O)CH3×4), 4.05-4.02 (m, 2H, H-6, H-6[1]), 4.44 (t, J6.6 Hz, 1H, H-5), 5.05 (dd, $J_{1,2}$3.9 Hz $J_{2,3}$10.9 Hz, 1H, H-2), 5.39 (dd, $J_{3,4}$3.3 Hz, $J_{2,3}$10.8 Hz, 1H, H-3), 5.50 (d, $J_{3,4}$3.2 Hz, 1H, H-4), 6.69 (d, $J_{1,2}$4 Hz, 1H, H-1).

Synthesis of 2-S-(2,3,4,6-tetra-O-acetyl-β-D-galactopyranosyl)-2-thiopseudourea

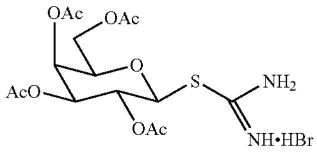

2,3,4,6-tetra-O-acetyl-α-D-galactopyranosyl bromide (37.5 g) dissolved in acetone (180 ml) with thiourea (10.9 g) at 25° C. Batch heated to reflux for a minimum of 2 hrs. Reaction followed by TLC (1:1 petrol/EtOAc. Starting material 0.69, plus multiple peaks below. Product is a salt and therefore seen on baseline (uv-active)). Batch cooled to R.T. and crystallised as a white crystalline solid (35 g, 79%) with the aid of petrol as anti-solvent. M.p=169-171° C. (Lit[3] 169° C.). $[\alpha]_D^{22}$+17 (EtOH, C=2.0) (Lit[3]+16). (1H NMR (DMSO, 400 MHz). δ=1.96, 2.02, 2.09, 2.14 (sx4, 4×3H, —C(O) CH3), 4.08-4.11 (m, 2H, H-6, H-6[1]), 4.4 (t, J6.2 Hz, 1H, H-5), 5.1 (t, $J_{2,3}$9.9 Hz, 1H, H-2), 5.2 (dd, $J_{2,3}$9.9 Hz, $J_{3,4}$3.4 Hz, 1H, H-3), 5.4 (d, J3.3 Hz, 1H, H-4), 5.6 (d, $J_{1,2}$10 Hz, 1H, H-1), 9.2 (Br, 4H, $2 \times NH_2$).

Synthesis of cyanomethyl 2,3,4,6-tetra-O-acetyl-β-D-thiogalactopyranoside

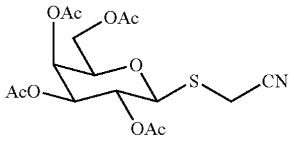 [SMILES: CC(=O)OCC1OC(SCC#N)C(OC(C)=O)C(OC(C)=O)C1OC(C)=O]

2-S-(2,3,4,6-tetra-O-acetyl-β-D-galactopyranosyl)-2-thiopseudourea hydrobromide (8.09 g), sodium metabisulphite (6.5 g), potassium carbonate (2.5 g) dissolved in acetone/water (50:50, 99 ml). To this solution chloroacetonitrile (4.4 ml) was added. Reaction was followed by TLC (1:1 petrol/ETOAc. starting material=0, product=0.55). Product crystallised by addition of ice-water (125 ml) to the reaction mixture, followed by a 2 hr age. Product filtered off as a white crystalline solid (6.1 g, 91%). Batch re-crystallised from hot MeOH. Product filtered as a white crystalline solid (2.4 g, 40%). M.p=95-97° C. (Lit[4] 95-97° C.). $[\alpha]_D^{22}$-57 ($CHCl_3$, C=1.0) (Lit[4]-30). $^1H$ NMR ($CDCl_3$, 200 MHz). δ=2.0, 2.0, 2.1, 2.1 (sx4, 4×3H, —C(O)CH3×4), 3.37 (d, J17 Hz, 1H, S—C<u>H</u>H), 3.66 (d, J17 Hz, 1H, S—CH<u>H</u>), 4.0 (t, J6.9 Hz, 1H, H-5), 4.1-4.2 (m, 2H, H-6, H-6[1]), 4.7 (d, $J_{1,2}$9.9 Hz, 1H, H-1), 5.1 (dd, $J_{3,4}$3.0 Hz, $J_{2,3}$10.1 Hz, 1H, H-3), 5.2 (t, J9.9 Hz, 1H, H-2), 5.5 (d, J2.1 Hz, 1H, H-4).

Synthesis of 1,2,3,4,6-penta-O-acetyl-D-mannopyranose

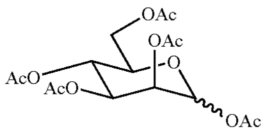 [SMILES: CC(=O)OCC1OC(OC(C)=O)C(OC(C)=O)C(OC(C)=O)C1OC(C)=O]

To Mannose (50 g, 0.128 mol), slurried in Acetic Anhydride (200 mL, 1.96 mol) a warn solution of Iodine (2.5 g) in Acetic anhydride (10 mL) was charged in portions (exothermic). Batch cooled in an ice-bath until exothermic reaction was completed. (TLC, Silica, 1:1 Petrol/EtOAc, product Rf: 0.47). Product extracted with DCM/10% Sodium Thiosulphate (1:1, 1 L). Organic layer quenched with a saturated solution of Sodium Bicarbonate. Organic layer dried with a saturated solution of Brine (3×200 ml) and Magnesium Sulphate. Batch evaporated to dryness under vacuum to afford a yellow/orange oil (96 g, 89%). $^1$HNMR (400 MHz, $CDCl_3$). δ=2.0, 2.0, 2.1, 2.1, 2.2, 2.2, 2.2, 2.2 (sx8, 3H×10, —C(O) CH3×8), 3.8 (m, 1H, H-5), 4.1 (1H, dd, $J_{5,6}$2.4 Hz, $J_{6,6}$ 12.4 Hz, H-6), 4.3 (dd, $J_{5,6}$5.4 Hz, $J_{6,6}$12.5 Hz, H-6[1]), 5.1 (dd, $J_{2,3}$3.4 Hz, $J_{3,4}$9.9 Hz, H-3), 5.3 (t, $J_{3,4}$9.3 Hz, 1H, H-4), 5.5 (dd, $J_{1,2}$1.3 Hz, $J_{2,3}$3.3 Hz, 1H, H-2), 5.9 (d, $J_{1,2}$1.1 Hz, 1H, βH-1), 6.1 (d, $J_{1,2}$1.9 Hz, 1H, αH-1)

Synthesis of 2-S-(2,3,4,6-tetra-O-acetyl-α-D-mannopyranosyl bromide

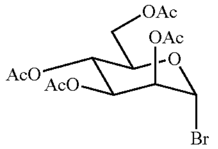 [SMILES: CC(=O)OCC1OC(Br)C(OC(C)=O)C(OC(C)=O)C1OC(C)=O]

1,2,3,4,6-penta-O-acetyl-D-mannopyranose (49 g) dissolved in HBr (33% in AcOH, 260 ml) with DCM (30 ml) as solvent aid. Reaction followed by TLC (Petrol:EtOAc 1:1) which showed reaction completion (Rf's: Starting material (0.46), product (multiple peaks, key peak at 0.69, multiple peaks possibly due to compound instability on silica and or hydrolysis by-products). Reaction took 2.5 hrs. Reaction mixture quenched with distilled water (1.4 L) followed by immediate extraction with DCM (3×350 ml). Organic layer neutralised with a saturated solution of Sodium Bicarbonate (3×1 L). Finally, organic layer dried with sodium sulphate and evaporated (maintaining the temperature<30° c.) to dryness under vacuum to afford an yellow oil (38.4 g, 74%).). $[\alpha]_D^{22}$+124 ($CHCl_3$, C=1.0) (Lit[5]+122). $^1H$ NMR (CDCl3, 400 MHz). δ=2.0, 2.0, 2.1, 2.2 (sx4, 3H x4, —C(O)CH3×4), 4.1 (dd, $J_{6,6}$12.6 Hz, $J_{5,6}$1.9 Hz, 1H, H-6), 4.2 (m, 1H, H-5), 4.3 (dd, $J_{6,6}$12.5 Hz, $J_{5,6}$4.9 Hz, 1H, H-6), 5.4 (t, $J_{3,4}$10.2 Hz, 1H, H-4), 5.5 (m, 1H, H-2), 5.7 (dd, $J_{3,4}$ 10 Hz, $J_{2,3}$3.4 Hz, 1H, H-3), 6.3 (s, 1H, H-1)1.

Synthesis of 2-S-(2,3,4,6-tetra-O-acetyl-α-D-mannopyranosyl-)-2-thiopseudourea hydrobromide

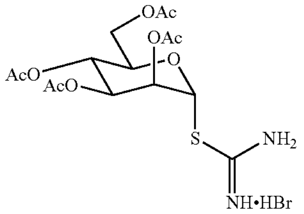

2-S-(2,3,4,6-tetra-O-acetyl-α-D-mannopyranosyl bromide (38 g) dissolved in acetone (180 ml) with thiourea (11 g) at 25° C. Batch heated to reflux for a minimum of 2 hrs. Reaction followed by TLC (1:1 petrol/EtOAc. Starting material 0.69, plus multiple peaks below. Product is a salt and therefore is seen on baseline (uv-active)). Batch cooled to R.T. and crystallised, as a white crystalline solid, with the aid of petrol as an anti-solvent (22 g, 49%). M.p=125-127° C. (Lit[6] 125-128° c.). $[\alpha]_D^{22}$+101 ($CHCl_3$, C=1.1) (Lit[6]+103). $^1$HNMR (400 MHz, DMSO). δ=2.0, 2.0, 2.0, 2.0 (sx4, 3H x4, —C(O)CH3×4), 4.1 (dd, $J_{6,6}$12.4 Hz, $J_{5,6}$2.3 Hz, 1H, H-6), 4.2 (dd, $J_{6,6}$12.4 Hz, $J_{5,6}$5.3 Hz, 1H, H-6'), 4.3 (m, 1H, H-5), 5.1 (dd, $J_{3,4}$10 Hz, $J_{2,3}$3.5 Hz, 1H, H-3), 5.2 (t, $J_{3,4}$9.9 Hz, 1H, H-4), 5.4 (dd, $J_{2,3}$3.4 Hz, $J_{1,2}$1.6 Hz, 1H, H-2), 6.3 (d, J1.3 Hz, 1H, H-1), 9.3 (s, 4H, 2×$NH_2$).

Synthesis of cyanomethyl 2,3,4,6-tetra-O-acetyl-α-D-thiomannopyranoside

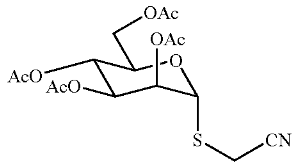 [SMILES: CC(=O)OCC1OC(SCC#N)C(OC(C)=O)C(OC(C)=O)C1OC(C)=O]

2-S-(2,3,4,6-tetra-O-acetyl-α-D-mannopyranosyl-)-2-thiopseudourea hydrobromide (5.9 g), sodium metabisulphite (4.8 g), potassium carbonate (1.8 g) dissolved in acetone/water (50:50, 75 ml). To this solution chloroacetonitrile (3.2 ml) was added. Reaction was followed by TLC (1:1 petrol/ETOAc. Starting material=0, Product=0.55) and has a reaction time of ~2 hrs. Product crystallised by addition of ice-water (100 ml) to the reaction mixture, followed by a 2 hr age. Product filtered off as a white crystalline solid (4.7 g, 96%) and recrystallised from hot MeOH (1.84 g, 40%). M.p=129-131° C. (Lit[4] 130-131° C.). $[\alpha]_D^{22}$+69 ($CHCl_3$, C=1.0) (Lit[4]+ 74.5) 1H NMR (CDCl3, 400 MHz). S=2.0, 2.1, 2.1, 2.2 (sx4, 4×3H, —C(O)CH3×4), 3.3 (d, J17.2 Hz, 1H, —SCH2C), 3.5 (d, J17.2 Hz, 1H, —SCH2C), 4.2 (dd, $J_{6,6}$10.1 Hz, $J_{5,6}$1.8 Hz, 1H, H-6$^1$), 4.3-4.4 (m, 2H, H-5, H6), 5.2 (dd, $J_{3,4}$10 Hz, $J_{2,3}$3.5 Hz, 1H, H-3), 5.4 (m, 1H, H-2), 5.5 (s, 1H, H-1).

EXAMPLES

Example 1

Glycosylation

Figure 2A:
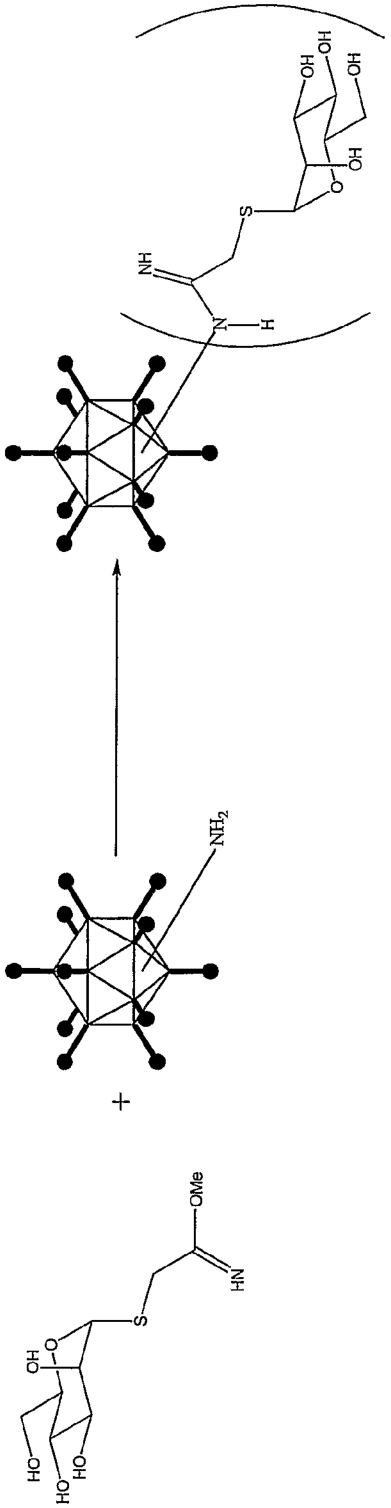
FIG. 2 illustrates that the glycosylation of adenovirus dramatically reduces transduction ability. A) Scheme where n=1-8000, B) effect of glycosylation in vitro on adenovirus usual transduction mechanism in CAR expressing A549 (lung carcinoma) cell lines. G-HIGH=highly modified with galactose, G-MED=partially modified with galactose, G-LOW=sparingly modified with galactose, repeated with mannose; C) ConA affinity for mannosylated structures. UNMOD=unmodified Ad, MM=$Man_M$-AV, MDM=$ManD_M$-AV, MH=$Man_H$-AV, MDH=$ManD_H$-AV; D) PNA affinity for galactosylated structures. UNMOD=unmodified Ad, GDM=$GalD_M$-AV, GDH=$GalD_H$-AV, 1=repeat of GDH on an unrefreshed column.
Figure 2B:
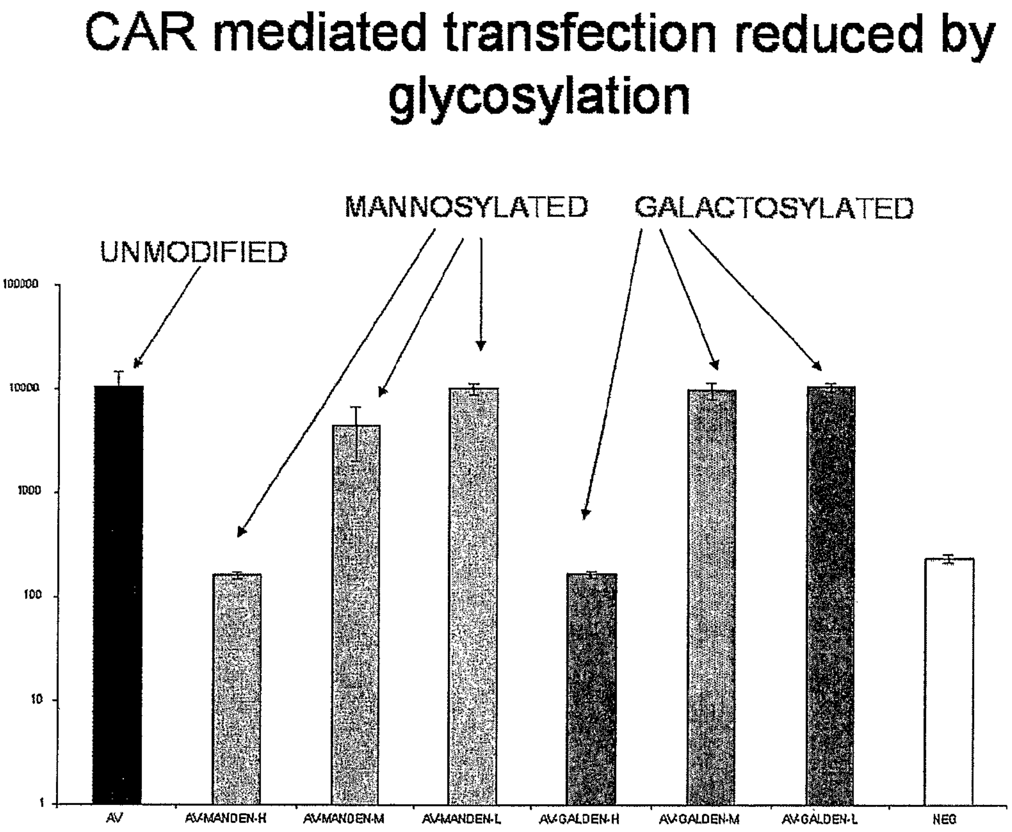

To determine the effect of glycosylation on adenovirus transfection via normal pathways, three different glycosylated structures were produced which represent highly (6000 equivalents of sugar per available lysine residue), partially (600 equivalents of sugar per available lysine residue) and sparingly (60 equivalents of sugar per available lysine residue) glycosylated structures. This has been achieved using 4 different glyco-structures to give a total of 12 constructs. Each was purified after glycosylation to remove excess reagent. As discussed earlier the 2-imino-2-methoxyethyl-1-thioglycoside reagent will glycosylate by nucleophilic attack of the primary amino group present in the lysine side chain of all adenovirus capsid proteins. Since lysine groups are required for effective interaction of adenovirus with CAR and membrane integrins we propose level of glycosylation will be proportional to transfection knockdown. This is demonstrated in FIG. 2*b* where a luciferase expressing adenovirus was used for assay. Lung carcinoma (A549) cells were used because of their high expression of the CAR receptor that makes them ideal for adenovirus in vitro analysis. Highly glycosylated particles show no significant transduction. We suggest that CAR and integrin binding has been dramatically disrupted.

Example 2

Characterisation of Glycosylation

Figure 3A:
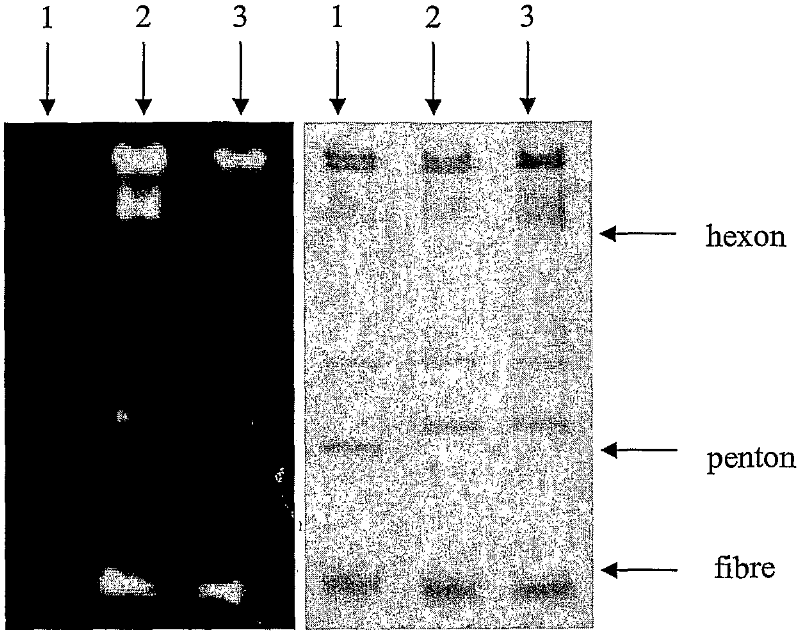
FIG. 3 illustrates the characterisation of chemical glycosylation by SDS-PAGE. A) left hand image shows glycoproteins by ProEmerald 488 stain. Right hand image shows the coomassie brilliant blue protein stain of left hand image. 1=unmodified virus, 2=galactosylated virus, 3=Mannosylated virus. B) Silver stain of an SDS PAGE for dendritic structures. 1=std, 2=$GalD_H$-AV, 3=$GalD_M$-AV, 4=GalDL-AV, 5=ManDH-AV, 6=ManDM-AV, 7=ManDL-AV, 8=AV, 9=MDHH-AV (10 uL of reagent charge at H equivalent). C) Focus on Hexon protein for three different levels of adenovirus chemical glycosylation with mannose. H=Highly glycosylated, M=Partially glycosylated, L=sparingly glycosylated, UNMOD=unmodified virus. A and B were run using Invitrogen NuPAGE™ 4-12% BIS-TRIS gel 1.0 mm×15 well pre-cast gels. C was run using a 6% Acrylamide gel. D) Sugar specificity by ConA affinity column.
Figure 3B:
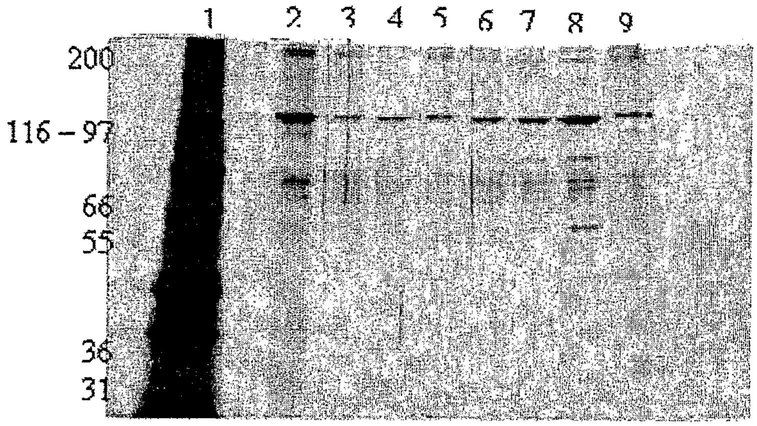
Figure 3C:
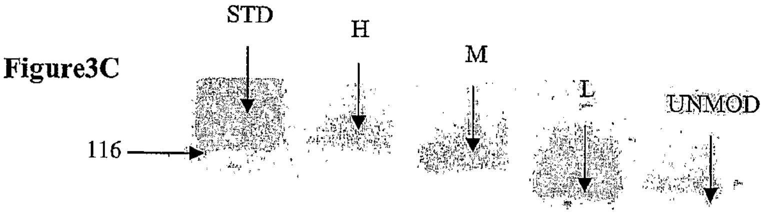
Figure 3D:
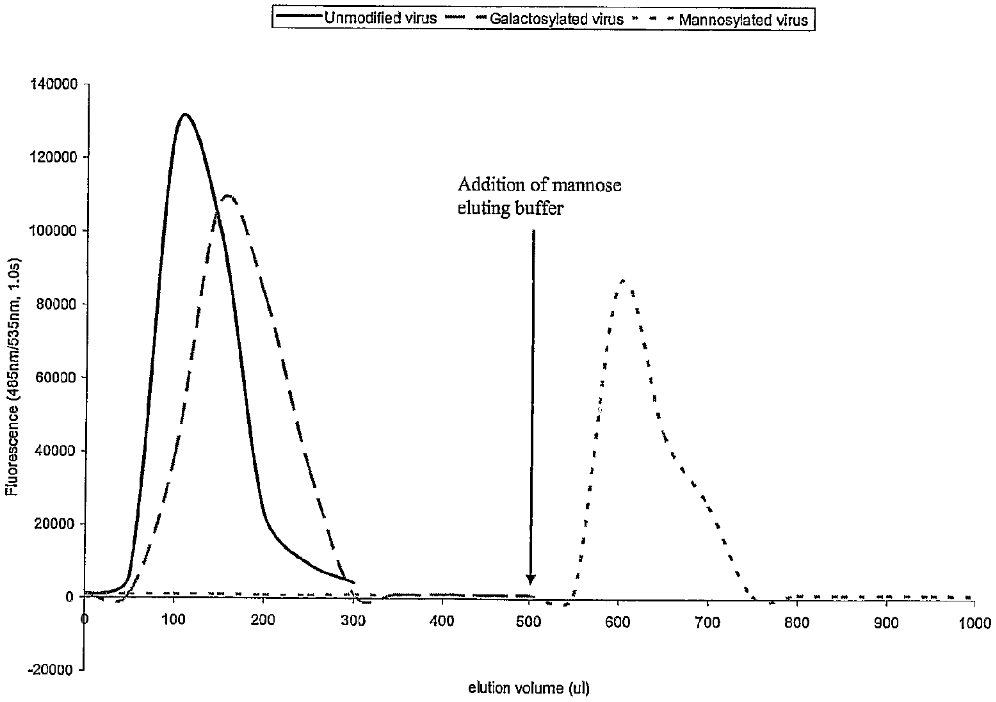

The adenovirus proteins have previously been characterised by SDS-PAGE.[11] By comparing the SDS-PAGE gel for an unmodified viral particle against the 12 modified types it was possible to determine where glycosylation was occurring on key capsid proteins (FIG. 3*b,c*). Heavily glycosylated virus showed significant protein mass differences for the Hexon, Penton base and Fibre proteins. To determine the presence of sugars a Periodic acid cleavage of diols followed by a Pro-Emerald stain (Purchased from Molecular Probes) was employed (FIG. 3*a*). By this stain the Hexon and Fibre proteins are easily visualised, although the Penton is less obvious. By comparing this to the coomassie stain perhaps this is not as surprising as there are different levels of glycosylation within the Penton viral sample. This coupled with a carbohydrate content close to the limit of detection may be responsible for the weak fluorescence seen. Indeed, this could indicate that other virus proteins which are sparingly glycosylated have not yet been detected by fluorescence, coomassie or silver stain. To distinguish between sugar modifications PNA and concanavalin A (ConA) lectin columns have been employed.

Concanavalin A

Figure 2C:
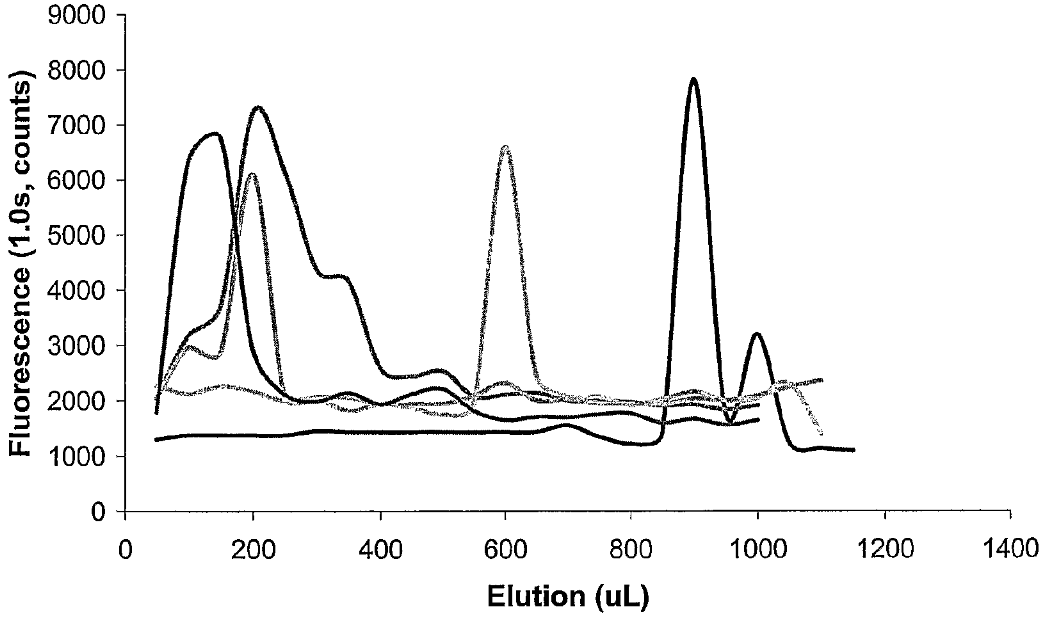

Concanavalin A has specificity for glucose<mannose<methyl mannose. Previously, $Man_H$-AV had been shown to have a high affinity for this lectin column, and no affinity for the unmodified or galactosylated structures. For this experiment the high and medium mannose monomer and dendrimer constructs have been analysed. Both MDH and MH show a good affinity. Excitingly the dendritic version shows an even stronger affinity. Perhaps this result helps to explain the 4 fold retargeting seen. Other points of interest are the appearance of what could be constructs with different levels of modification within one sample. This is shown for MDH, MDM and to a smaller degree MM and MH. It is unlikely that these peaks come from particle degradation since analysis is by picogreen which analyses DNA (not protein concentration). It is also unlikely that they are due to free DNA in the sample since this is removed during purification after modification. This is illustrated in FIG. 2C.

PNA

Figure 2D:
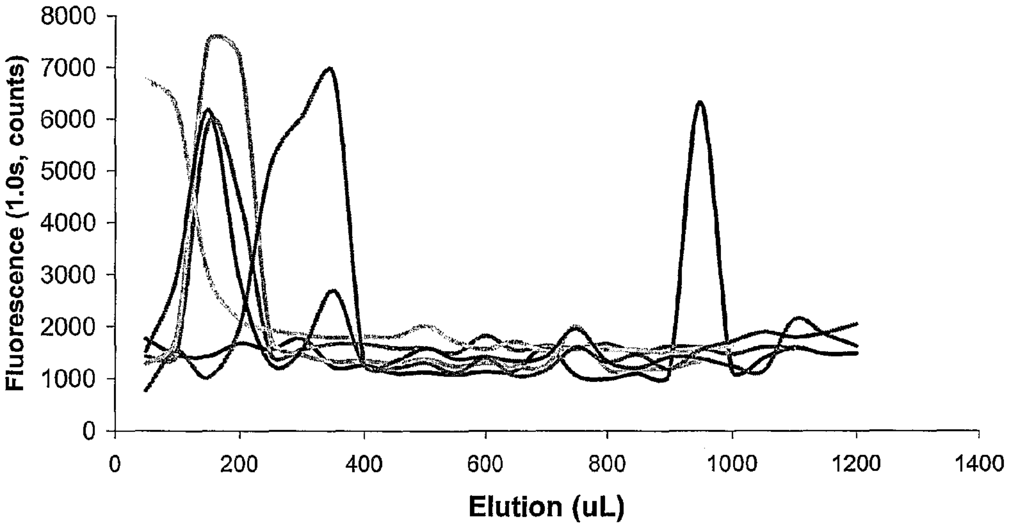

To analyse the galactosylated constructs a peanut agglutinin lectin was used. FIG. 8 shows the first data set with the dendritic structures. A strong affinity is shown for GDH, however GDM shows very little affinity. This is actually a nice result which tally's with the level of modification seen. Sample 1 is a repeat GDH on a column which had not been regenerated. Very little affinity is shown which suggests that the affinity seen on a fresh column is due to the interaction of the sugars with the bound lectins. This is illustrated in FIG. 2D.

Quantification of levels of dendritic and monomeric glycosylation is illustrated in Table 1 and 2.

Example 3

Virus Integrity

Adenoviral capsid proteins exist as homodimers or homotrimers held together by ionic interactions which can be disrupted easily by addition of detergent such as Sodium dodecylsulphate (SDS) or guanidine chloride. We asked the question does glycosylation lead to destruction of the adenovirus capsid and/or does glycosylation lead to agglomeration? We considered this unlikely since spin column purification would remove degraded viral particles; however we had noticed smaller yields being recovered for modified particles. To fully characterise the glycosylation we decided to investigate this question using a novel approach to PicoGreen analysis, size exclusion HPLC, photon correlation spectrometry (PCS) and Zeta potential. PicoGreen analysis is routinely used to indirectly calculate the number of viral particles present in solution. It works by conjugating to DNA which can be measured by fluorescence spectroscopy. This technique has the advantage of high sensitively which is useful when protein concentrations are to low for accurate analysis as is the case with adenoviral titres. In order for PicoGreen to conjugate to viral DNA the virus capsid must be dissociated so that DNA is exposed. This is often done using the detergent SDS. We propose that PicoGreen analysis performed on whole viral particles will show only background fluorescence. By comparing the viral sample after glycosylation with the unglycosylated batch we are able to determine the effect of glycosylation on adenovirus structure. This is shown in FIG. 3*a*. This figure suggests viral integrity is sustained after glycosylation, and spin column purification removes the significant amount of degraded particles present in both samples. We considered that glycosylation may led to disruption that does not led to exposure of DNA. To test this we compare size exclusion HPLC spectra for purified modified and unmodified samples (FIG. 3*b*). Predictably no difference in retention time is seen. Pleasingly, integrated absorbance intensities positively compare to PicoGreen titres recorded and removal of excess glycosylation reagent was also confirmed using this technique. PCS was used to look for possible aggregation of virus particles after modification. Interestingly this showed an increase in diameter of approx 80 nm. This increase in size would be consistent with the diameter of adenovirus including the protruding fibre proteins since these proteins are not usually detected by PCS. We propose that glycosylation of adenovirus fibre significantly effects how particles move in solution effectively lighting up fibre proteins. A comparable charge was seen by zeta potentiometry as expected. Similar results have been obtained for dendritic structures.

Example 4

In vitro Transduction and Retargeting

Figure 4A:
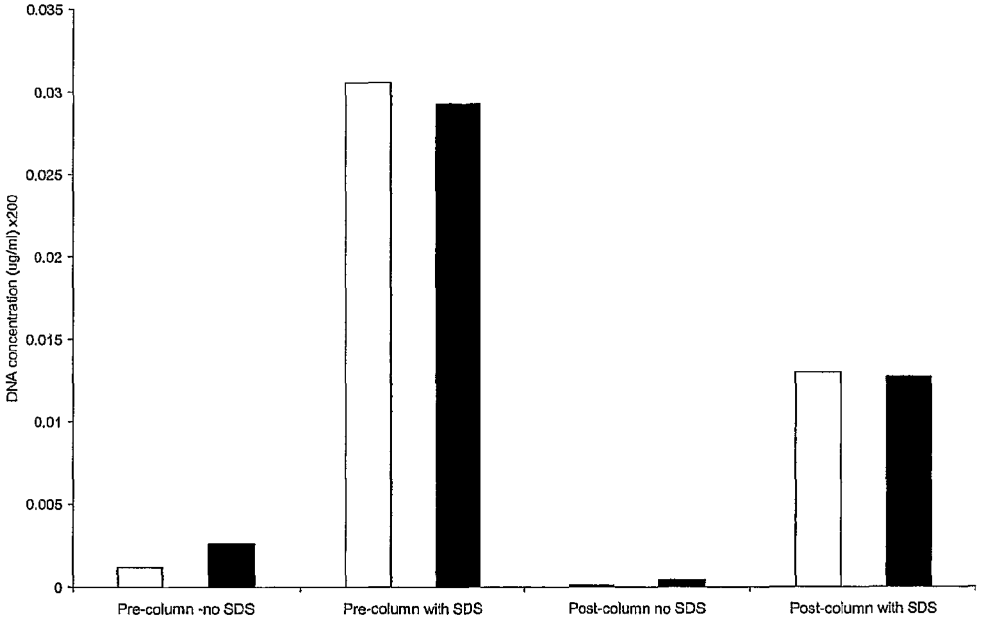
FIG. 4 illustrates that virus integrity is maintained after glycosylation. A) PicoGreen analysis reveals viral DNA remains contained, white bar=unmodified, black bar=modified. B) Retargeting of mannosylated dendritic structures shows a four fold increase over the monomer. C) PCS reveals an untrue increase in size and D) zeta potential is comparable.
Figure 4B:
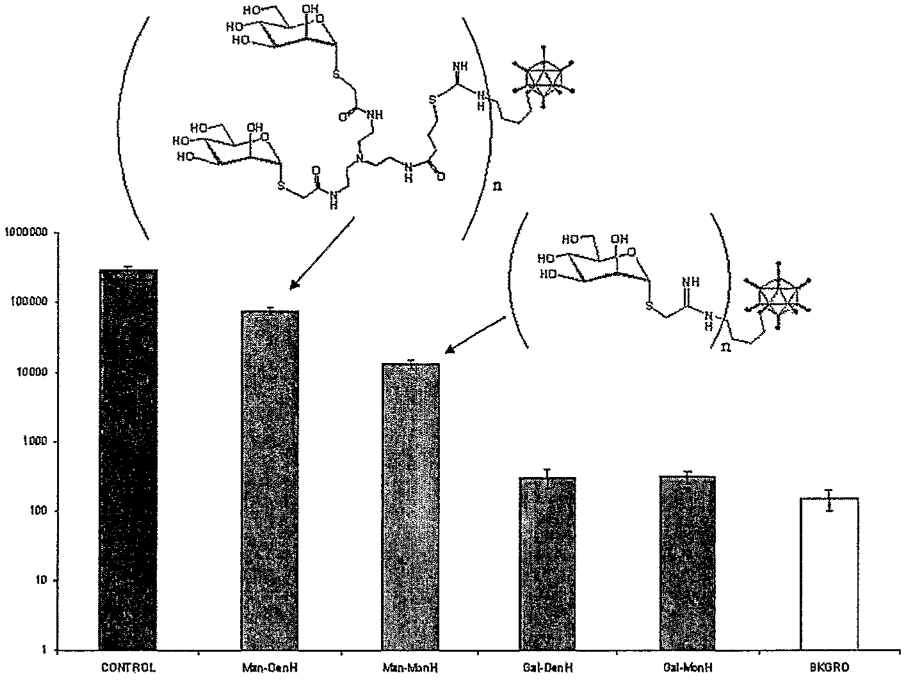
Figure 5:
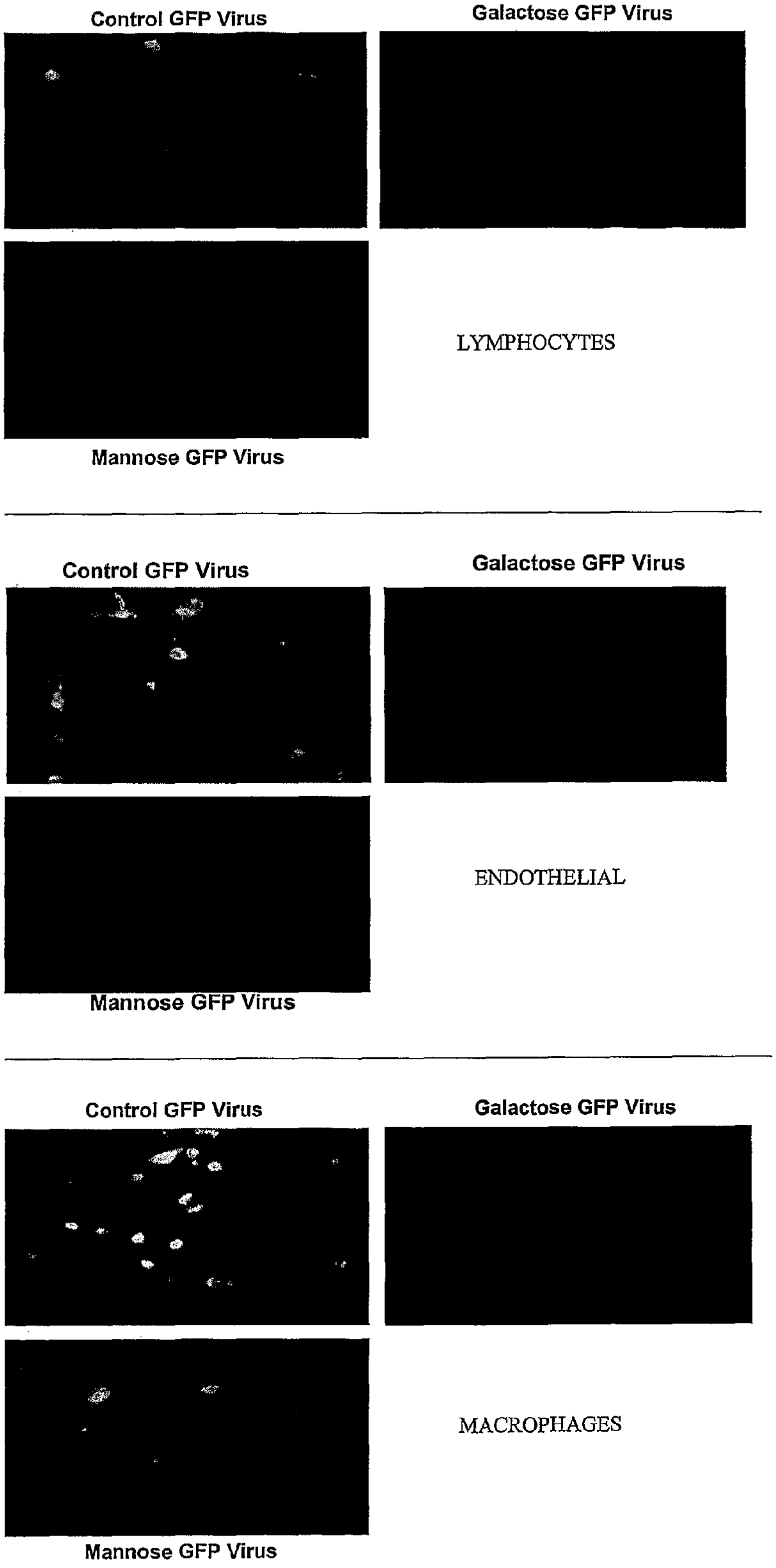
FIG. 5 illustrates that retargeting of mannosylated adenovirus is selective for macrophages that express the mannose receptor. Unmodified virus is used as a positive control and galactosylated virus as a negative control.

To this point we have shown that glycosylation of adenovirus occurs on all three major capsid proteins, that virus integrity is sustained and glycosylation is proportional to the degree of transfection knockdown on A549 cell lines. One question remained for us to answer. Is knockdown really due to CAR and integrin binding disruption or is it due to glycosylation of internal proteins effectively killing adenovirus replication at some stage after infection or is it both? To answer this question we transduced lymphocytes, known to be CAR deficient, macrophages, which are CAR deficient but express a mannose specific receptor, and endothelial cells which express CAR. Our hypothesis was: mannosylated particles will be unable to significantly transduct mannose receptor deficient lymphocytes and endothelial cells since both integrin and CAR binding is disrupted. Transduction will be seen on macrophages via the mannose receptor and not via integrin binding. Unmodified and galactosylated particles were used as negative controls. GFP and luciferase virus was used as an assay system. Lymphocytes were used as a negative control to show that no transfection is achieved by modified or unmodified virus. This is shown in FIG. 4*a*. Endothelial cells, which are known to express CAR, were used to show knockdown of modified particles shown in FIG. 4*b*. Galatose modified particles show no transduction of macrophages. Unmodified particles did show high transduction which is proposed to occur via integrin binding. Mannosylated particles did show a significant amount of transduction which we propose occurs via carbohydrate-protein interaction at the mannose receptor. Transduction by mannosylated particles in macrophages shows a lower order of magnitude compared to unmodified particles. We propose this is due to infection via integrin binding being more effective than via the mannose receptor.

The increased luciferase expression seen in the dendritic structure is equivalent to a 4 fold increase. Speculation on why these structures show increased retargeting is 3 fold. 1. Divalent effect increases the binding affinity or avidity. 2. The amide backbone provides a spacer which aids binding. 3. Less modification of internal proteins due to size. Point 3 has no founding data and no characterisation so far has ever provided evidence for it. It does remain an interesting point to consider. Greber has shown in many publications the intricate way in which Ad 5 transfects cells and has shown how minor alterations to the vector can have large implications into vector transfection.

As before, no targeting is seen for the galactosylated structures. Monocytes or macrophages are not thought to contain a galactose receptor. This data, although negative, goes some way to arguing against point 3 since the galactose dendrimer structures show no luciferase expression.

Example 5

The display of lysine residues on the Ad capsid seen by crystal structure is thought to be patchy and unevenly spread out over the surface. This must mean that portions of the capsid will not display the modification and so antibody binding will occur. From this it is unlikely that the current modifications will have an impact on antibody binding. To investigate this a primary polyclonal antibody from rabbit serum was used, which is known to bind epitopes. A rabbit-goat secondary antibody was used which on treatment with ECL reagent would chemifluoresce.

Figure 6A:
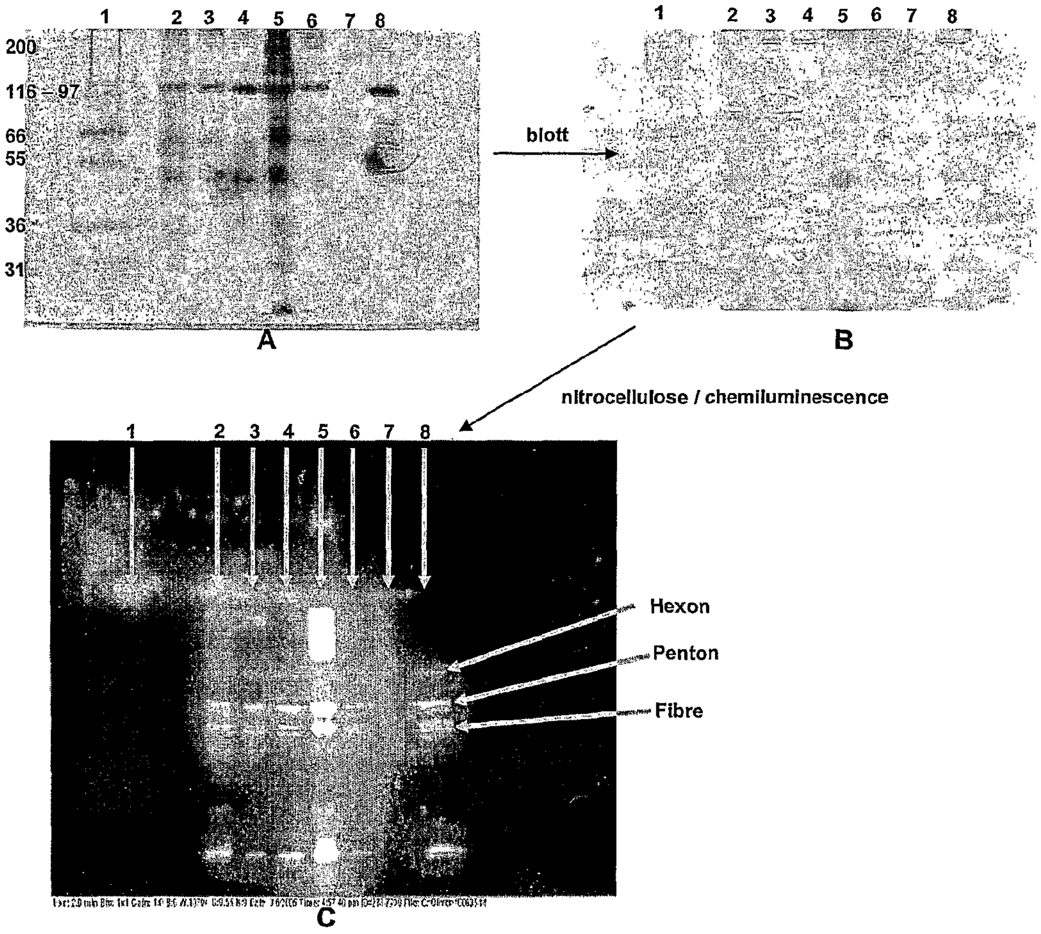
FIG. 6A. Antibody binding to monomer modified adenovirus. Panel A, silver stain of constructs, virus batch, virus concentration and sample volume were constant for each; panel B, silver stain of blotted PAGE; panel C, nitrocellulose blot of B using a rabbit-goat 2Ab then ECL. 1=mass marker, 2=$Gal_H$-AV, 3=$Gal_M$-AV, 4=$Gal_L$-AV, 5=$Man_H$-AV, 6=$Man_M$-AV, 7=$Man_L$-AV, 8=AV.
Figure 6B:
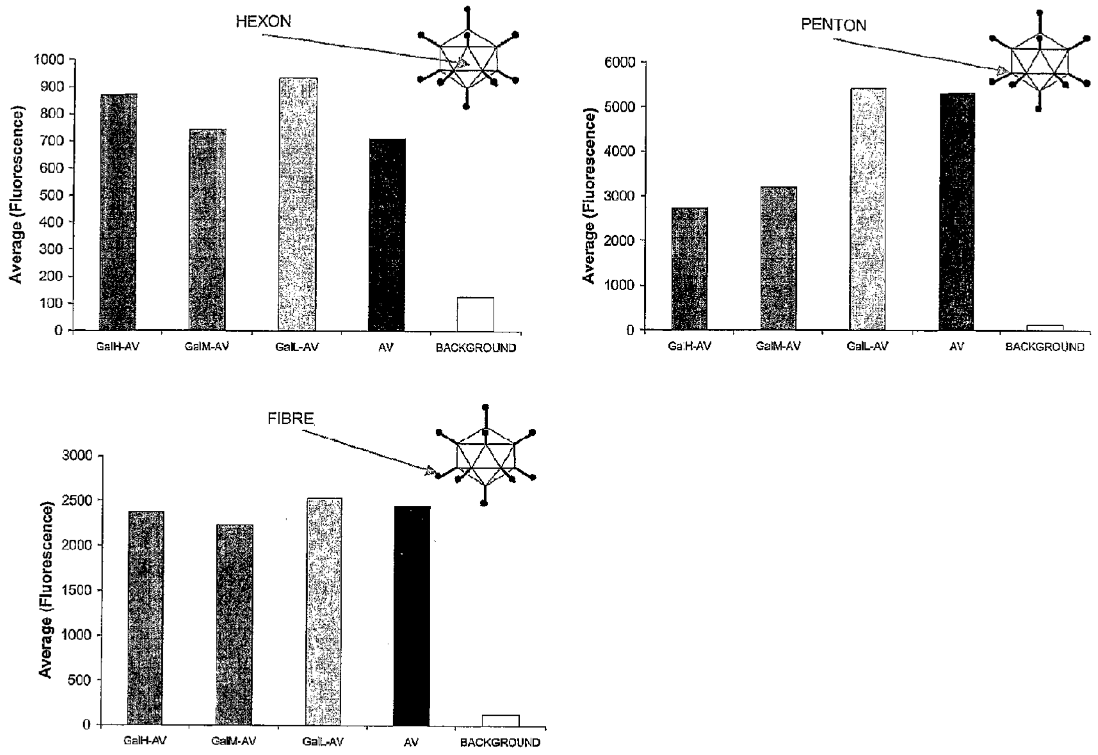
FIG. 6B. Intensity of antibody binding on monomer structures. Hexon and fibre show no significant difference. Penton shows an interesting correlation between level of modification and level of antibody binding.

All twelve structures were investigated. Their titres were calculated and their concentrations corrected so that a consistent volume added to the gel should contain the same amount of protein. The ratio between protein and DNA present in Ad batches also varies, sometimes significantly. The same batch of Ad was used in this work to remove this variable. With that in mind the data recorded can be considered quantitative. The monomer modified structures were investigated first and this data is shown in FIG. 6*a* and FIG. 6*b*.

The silver stain 3A reveals a miscalculation in titre for 7 ($Man_L$-AV). The silver stain 3B was used to determine the efficiency of transfer of proteins onto the nitrocellulose. Because of the size of Ad proteins the transfer was run for 15 hr. The antibody bound nitrocellulose blot 3C revealed that the key capsid proteins were still available for antibody binding. Because a consistent amount of protein was charged for each construct onto the PAGE (revealed by comparison of hexon in 3A and 3B) the level of antibody binding was analysed quantitatively. This is shown in FIG. 4.

Figure 6C:
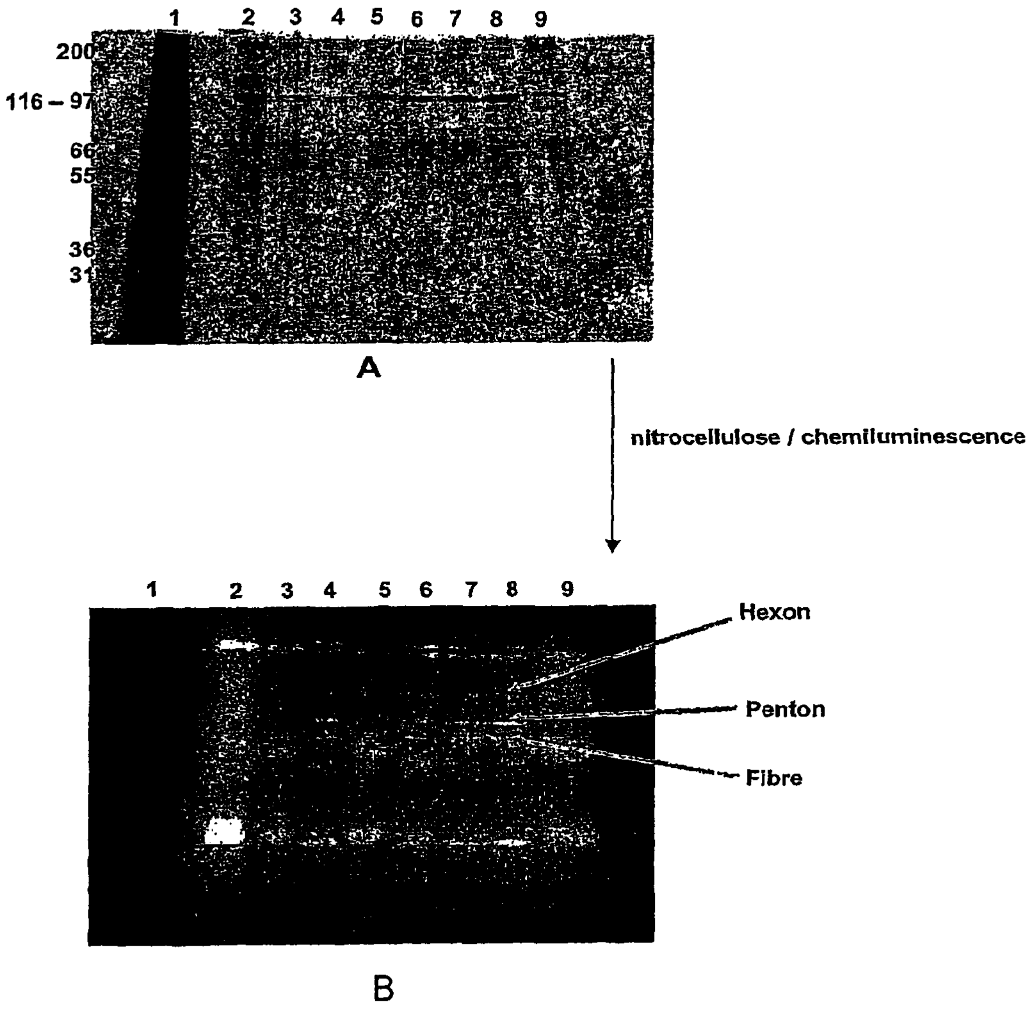
FIG. 6C. Dendrimer antibody staining. Panel A, Silver stain of an SDS PAGE; panel B, Nitrocellulose blott viewed using ECL and chemiluminescence. 1=std, 2=GalDH-AV, 3=GalDM-AV, 4=GalDL-AV, 5=ManDH-AV, 6=ManDM-AV, 7=ManDL-AV, 8=AV, 9=MDHH-AV.
Figure 6D:
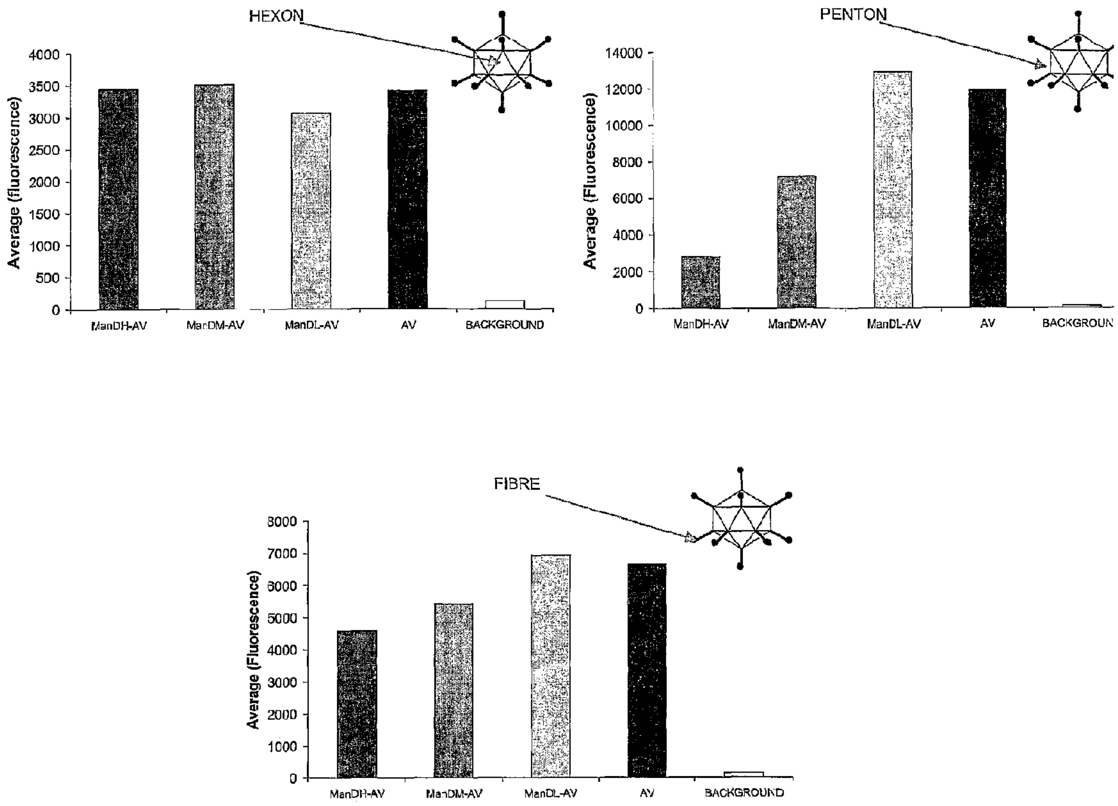
FIG. 6D Intensity of antibody binding on Dendrimer structures. Hexon show no significant difference. Penton and fibre shows an interesting correlation between level of modification and level of antibody binding and make an interesting comparison with their monomer counterparts.

Hexon and fibre show no significant difference in antibody binding between modified and unmodified samples. Penton shows a significant decrease in antibody binding for modified structures which is proportional to the level of modification. If we consider the location of penton on the capsid we see that it may be hindered in terms of antibody binding with respect to the other two major proteins. Therefore a small modification may explain the binding inhibition seen. This interesting result was explored further using the six dendritic constructs. The experiment was run as for the monomer constructs. FIG. 6*c* and FIG. 6*d* summarise the results.

Once again no decrease in intensity from antibody binding was seen for hexon. Penton did show decrease in binding that correlates to the level of modification and this was significantly more prominent than was seen for the monomer modification. Fibre also showed a significant decrease in antibody binding which again correlates to the level of modification. This was not seen for the monomer modified constructs. This data is very exciting. There are no examples where the individual modified Ad capsid proteins have been analysed for antibody binding. This could prove an excellent technique when analysing the larger modifications.

1 REFERENCES 1.
   a. Grimm, D.; Kay, M, A. Curr. Gene Ther. 2003, 3, 281
   b. Thomas, E. K; Ehrhardt, A; Kay, M. A. Nat. Rev. Genet. 2003, 4, 346
2. Zamecnik, P. C.; Raychowdhury, M. K.; Tabatadze, D. R.; Cantiello, H. F. Proc. Natl. Acad. Sci. U.S.A. 2004, 101, 8150
3. Xu R.; Li H.; Lai-yin T.; Hsiang-fu K.; Lu H.; Lam K. S. L. Curr. Gene Ther. 2003, 3, 65
4. Kanerva, A.; Hemminki, A. Int. J. Cancer, 2004, 110, 475
5. Volpers, C.; Kochanek, S. J Gene Med, 2004, 6, S164
6. San-Martin, C.; Burnett, R. M. Current topics in microbiology and immunology, 2003, 274, 57
7. Meier, O.; Greber, U. F. J Gene Med, 2004, 6, S152
8. Gabius, H.; Siebert, H.; Andre, S.; Jimenez-Barbero, J.; Rudiger, H. ChemBioChem, 2004, 5, 740-764
9.
   a. Stowell, C. P.; Lee Y. C. Methods Enzymol. 1982, 83, 278
   b. Roger, R.; Neilson, D. G. Chem. Rev. 1961, 61, 179
10. van Raaij, M. J.; Mitraki, A.; Lavigne, G.; Cusack, S, Nature, 1999, 401, 935
11. j Lee, Y. C.; Stowell, C. P.; Krantz, M. J. Biochemistry, 1976, 15, 395.

2 REFERENCES

Additional Experimental

1. Pozsgay, V.; Jennings, H. J. Synthesis, 1990, 80, 724
2. Zhang, Z.; Magnusson, G. Carbohydr. Res. 1996, 295, 41
3. Bonner, W. A.; Kahn, J. E. J. Am. Chem. Soc. 1951, 73, 2241
4. Lee, Y. C.; Stowell, C. P.; Krantz, M. J. Biochemistry, 1976, 15, 3956
5. Micheel, F.; Micheel, H. Chem. Ber. 1930, 63, 386
6. Durette, P. L.; Shen, T. Y. Carbohydr. Res. 1980, 81, 261
7. Website: www.probes.com, January 2004.
8 Graziani-Bowering, G. M.; Graham, J. M.; Filion L. G. J Immunol Methods. 1997, 207, 15

TABLE 1

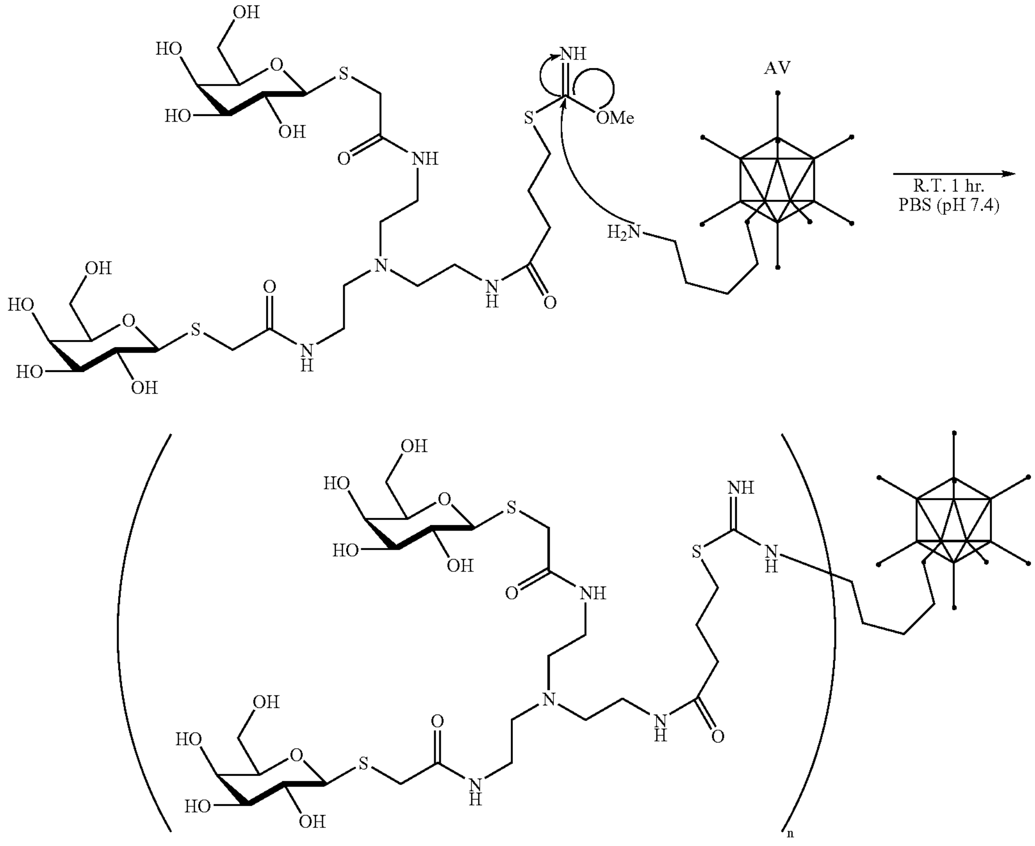

| Protein | Number of repeats/virus | Est. number of lysine residues | Est. numbers of sugars/protein | | |
|---|---|---|---|---|---|
| | | | H | M | L |
| Fibre | 24 | 15 | 6 | 2 | N/D |
| Penton | 12 | 20 | 12 | N/D | N/D |
| Hexon | 720 | 30 | 28 | 2 | N/D |
| Total (n) | | 22200 | 20010 ± 700 | 1490 ± 300 | N/D |

TABLE 2

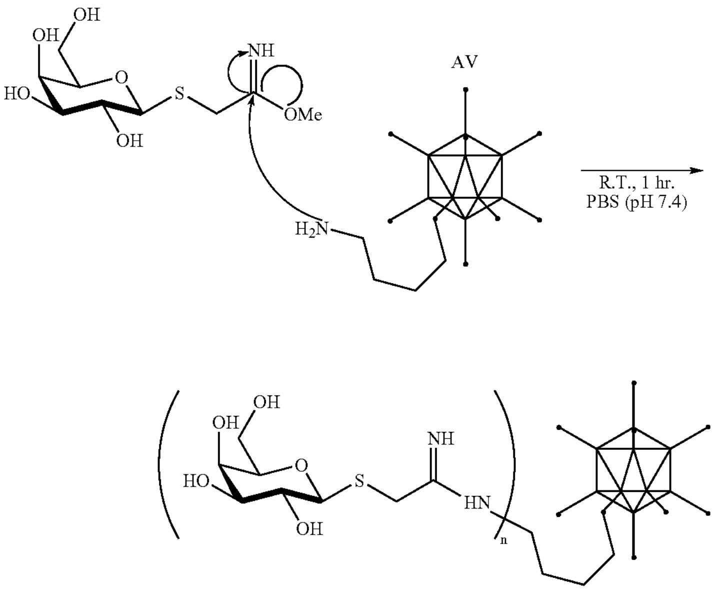

| | | | Est. numbers of sugals/protein | | |
|---|---|---|---|---|---|
| Protein | Number of repeat/virus | Est. number of lysine residues | H | M | L |
| Fibre | 24 | 15 | 14 | 5 | 2 |
| Penton | 12 | 20 | 14 | 3 | ND |
| Hexon | 720 | 30 | 28 | 12 | 2 |
| Total (n) | | 22200 | 20700 = 700 | 8800 ± 300 | 1490 ± 40 |

The invention claimed is:

1. An adenovirus particle modified by in vitro treatment with a chemical or enzymatic reagent, comprising a fibre protein modified to comprise at least two sugar pendent groups.

2. An adenovirus particle according to claim 1 wherein the fibre comprises 2 to 14 sugar pendent groups.

3. An adenovirus particle according to claim 1 comprising:

a penton comprising one or more sugar pendent groups, a hexon comprising one or more sugar pendent groups, or a penton comprising one or more sugar pendent groups and a hexon comprising one or more sugar pendent groups.

4. An adenovirus particle according to claim 1, wherein a viral capsid polypeptide is modified by addition of a sugar pendent group at a lysine residue.

5. An adenovirus particle according to claim 1, wherein the viral capsid polypeptide is modified by chemical means.

6. An adenovirus particle according to claim 1 wherein the particle is replication competent.

7. An adenovirus particle according to claim 1 comprising a penton comprising at least one sugar pendent group.

8. An adenovirus particle according to claim 1 which comprises 1490+/−300 sugar pendent groups.

9. An adenovirus particle according to claim 8 which comprises 20700+/−700 sugar pendent groups.

10. A viral particle according to claim 1 which is modified by chemical treatment, wherein the chemical treatment comprises reacting the viral particle with one of:

1,2,3,4,6-penta-O-acetyl-β-D-galactopyranose

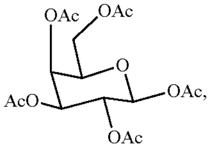 [SMILES: CC(=O)OCC1OC(OC(C)=O)C(OC(C)=O)C(OC(C)=O)C1OC(C)=O]

, 2,3,4,6-tetra-O-acetyl-α-D-galactopyranosyl bromide

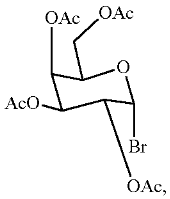 [SMILES: CC(=O)OCC1OC(Br)C(OC(C)=O)C(OC(C)=O)C1OC(C)=O]

,

2-S-(2,3,4,6-tetra-O-acetyl-β-D-galactopyranosyl)-2-thiopseudourea

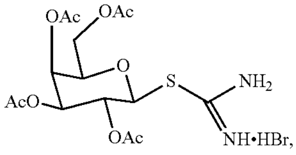

, 2,3,4,6-tetra-O-acetyl-β-D-thiogalactopyranoside

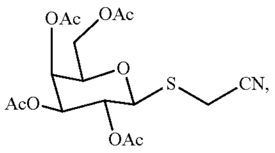 [SMILES: CC(=O)OCC1OC(SCC#N)C(OC(C)=O)C(OC(C)=O)C1OC(C)=O]

1,2,3,4,6-penta-O-acetyl-D-mannopyranose

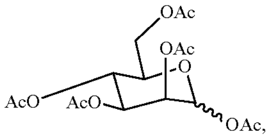 [SMILES: CC(=O)OCC1OC(OC(C)=O)C(OC(C)=O)C(OC(C)=O)C1OC(C)=O]

2-S-(2,3,4,6-tetra-O-acetyl-α-D-mannopyranosyl bromide

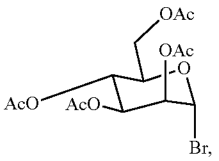 [SMILES: CC(=O)OCC1OC(Br)C(OC(C)=O)C(OC(C)=O)C1OC(C)=O]

2-S-(2,3,4,6-tetra-O-acetyl-α-D-mannopyranosyl)-2-thiopseudourea hydrobromide

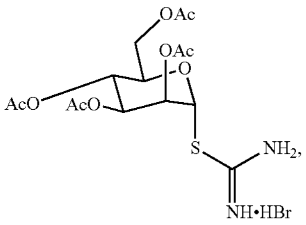

or 2,3,4,6-tetra-O-acetyl-α-D-thiomannopyranoside

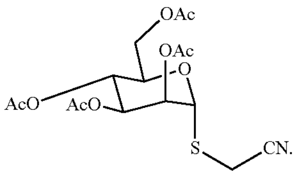 [SMILES: CC(=O)OCC1OC(SCC#N)C(OC(C)=O)C(OC(C)=O)C1OC(C)=O]

11. A modified viral particle according to claim 10, wherein a viral capsid polypeptide is modified by addition of said sugar group at a lysine residue.

12. A modified viral particle according to claim 10 wherein the particle is replication competent.

* * * * *